United States Patent
Li et al.

(10) Patent No.: US 9,850,520 B2
(45) Date of Patent: Dec. 26, 2017

(54) ELECTROCHEMICAL DETECTION OF PROTEASES USING AC VOLTAMMETRY ON NANOELECTRODE ARRAYS

(71) Applicant: Kansas State University Research Foundation, Manhattan, KS (US)

(72) Inventors: Jun Li, Manhattan, KS (US); Duy Hua, Manhattan, KS (US); Lateef Uddin Syed, Portland, OR (US); Allan Prior, Manhattan, KS (US); Luxi Swisher, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 210 days.

(21) Appl. No.: 14/320,215

(22) Filed: Jun. 30, 2014

(65) Prior Publication Data
US 2015/0011421 A1    Jan. 8, 2015

Related U.S. Application Data

(60) Provisional application No. 61/842,457, filed on Jul. 3, 2013.

(51) Int. Cl.
| | |
|---|---|
| G01N 15/06 | (2006.01) |
| G01N 33/00 | (2006.01) |
| G01N 33/48 | (2006.01) |
| C12Q 1/37 | (2006.01) |
| B01J 19/00 | (2006.01) |
| G01N 27/27 | (2006.01) |
| G01N 27/30 | (2006.01) |
| B82Y 15/00 | (2011.01) |

(52) U.S. Cl.
CPC ............ *C12Q 1/37* (2013.01); *B01J 19/0046* (2013.01); *G01N 27/27* (2013.01); *G01N 27/308* (2013.01); *B01J 2219/00653* (2013.01); *B01J 2219/00659* (2013.01); *B01J 2219/00725* (2013.01); *B82Y 15/00* (2013.01); *G01N 2333/96466* (2013.01); *G01N 2800/7028* (2013.01)

(58) Field of Classification Search
CPC ......... G01N 15/06; G01N 33/00; G01N 33/48
USPC ....... 422/50, 68.1, 82.01, 82.02; 436/43, 63, 436/64; 977/700, 702, 704, 705, 721, 977/723, 788, 789, 790, 953, 957, 958, 977/959
See application file for complete search history.

(56) References Cited

U.S. PATENT DOCUMENTS

| | | | | |
|---|---|---|---|---|
| 7,635,423 | B2 * | 12/2009 | Boussaad et al. | 205/777.5 |
| 7,638,036 | B2 * | 12/2009 | Boussaad et al. | 205/777.5 |
| 7,670,831 | B2 * | 3/2010 | Lee et al. | 435/283.1 |
| 7,939,734 | B1 * | 5/2011 | Li et al. | 435/6.1 |
| 8,597,492 | B2 * | 12/2013 | Choi et al. | 205/792 |
| 8,877,518 | B2 * | 11/2014 | Bau et al. | 436/524 |

(Continued)

*Primary Examiner* — Brian J Sines
(74) *Attorney, Agent, or Firm* — Hovey Williams LLP

(57) ABSTRACT

An electrochemical method for measuring the activity of enzymes using nanoelectrode arrays fabricated with vertically aligned carbon nanofibers. Short peptide substrates specific to disease-related enzymes are covalently attached to the exposed nanofiber tips. A redox moiety, such as ferrocene, can be linked at the distal end of the nanofibers. Contact of the arrays with a biological sample containing one or more target enzymes results in cleavage of the peptides and changes the redox signal of the redox moiety indicating the presence of the target enzymes.

11 Claims, 8 Drawing Sheets

(56) References Cited

U.S. PATENT DOCUMENTS

| | | | | |
|---|---|---|---|---|
| 8,888,969 | B2* | 11/2014 | Soleymani et al. | 204/289 |
| 8,920,619 | B2* | 12/2014 | Salzer et al. | 204/403.03 |
| 2002/0172963 | A1* | 11/2002 | Kelley | B01J 23/75 |
| | | | | 506/39 |
| 2005/0230270 | A1* | 10/2005 | Ren et al. | 205/777.5 |
| 2007/0227906 | A1* | 10/2007 | Boussaad | B82Y 15/00 |
| | | | | 205/777.5 |
| 2007/0278111 | A1* | 12/2007 | Boussaad | B82Y 15/00 |
| | | | | 205/792 |
| 2009/0061451 | A1* | 3/2009 | Achim | C12Q 1/003 |
| | | | | 435/6.11 |
| 2009/0278556 | A1* | 11/2009 | Man | G01N 27/4146 |
| | | | | 324/693 |
| 2009/0283424 | A1* | 11/2009 | Carson | B82Y 5/00 |
| | | | | 205/792 |
| 2010/0285514 | A1* | 11/2010 | Claussen | C12Q 1/006 |
| | | | | 435/25 |
| 2011/0163296 | A1* | 7/2011 | Pace | B82Y 15/00 |
| | | | | 257/24 |
| 2012/0125771 | A1* | 5/2012 | Salzer | G01N 27/308 |
| | | | | 204/412 |

* cited by examiner (SEQ ID NO:2)
= H₂N-(CH₂)₄-CO-Leu-Arg-Phe-Gly-NH-CH₂-Fc

ELECTROCHEMICAL DETECTION OF PROTEASES USING AC VOLTAMMETRY ON NANOELECTRODE ARRAYS

CROSS-REFERENCE TO RELATED APPLICATION

This application claims the benefit of U.S. Provisional Patent Application No. 61/842,457, filed Jul. 3, 2013, which is incorporated by reference herein in its entirety.

STATEMENT REGARDING FEDERALLY SPONSORED RESEARCH OR DEVELOPMENT

This invention was made with U.S. Government support under grant number R15CA159250 awarded by the National Institutes of Health. The government has certain rights in the invention.

SEQUENCE LISTING

The following application contains a sequence listing in computer readable format (CRF), submitted as a text file in ASCII format entitled "SequenceListing," created on Jun. 30, 2014 as 2 KB. The content of the CRF is hereby incorporated by reference.

BACKGROUND OF THE INVENTION

Field of the Invention

The present invention is generally directed toward an electrochemical method for measuring the activity of proteases using nanoelectrode arrays (NEAs) fabricated with vertically aligned carbon nanofibers (VACNFs). Short peptide substrates specific to disease-related enzymes are covalently attached to the exposed VACNF tips of the NEAs. A redox moiety, such as ferrocene (Fc), can be linked at the distal end of the CNFs. Upon being exposed to a biological sample containing one or more target enzymes, the change in redox signal of the redox moiety due to cleavage of the peptides can be measured using AC voltammetry (ACV) thereby indicating the presence of a specific target enzyme in the sample.

Description of the Prior Art

Globally, it was estimated that about 7.6 million people died in 2007 from various types of cancer, translating into about 20,000 people that die every day. Early diagnosis via cost-effective screens on the high-risk subpopulation is the key for saving millions of lives. Early diagnosis and objective monitoring of treatment response are key components in cancer diagnosis, therapeutic treatment, and integrated management. It has been known that the overexpression of various enzymes such as kinases, phosphatases, and proteases leads to cancers. Cancer metastasis is an uncontrollable cell growth through invasion to neighboring cells and activation of oncogenic pathways. The invasive process particularly involves proteases, a group of enzymes that cause proteolysis to degrade the extracellular matrix components and intercellular cohesive structures of neighboring cells leading to the activation of growth and angiogenic factors. Many clinical therapeutics or drugs under clinical development are based on kinase and protease inhibitors.

Proteases overexpressed in cancer cells and secreted into circulation are not only present as drug targets for the development of protease inhibitors, but also as biomarkers for diagnosis. Three proteases highly expressed in tumors, tumor-associated endothelial cells, tumor-associated macrophages, and other stromal cells are legumain, cathepsin B, and matrix-metalloproteinase 7 (MMP-7). The cysteine protease legumain has a strict specificity for hydrolysis of asparaginyl bonds. It is highly expressed in the metastatic and invasive solid tumors, where it activates other proteases such as cathepsin B, H and L, leading to elastolytic and collagenolytic activities. Although basal proteases are found in normal macrophages, overexpression of these cysteine proteases has not been found in normal tissues. Legumain is found highly expressed in a majority of tumors including carcinomas of the breast, colon, and prostate, and in central nervous system neoplasms. Cathepsin B is overexpressed in various cancers including esophageal adenocarcinoma, breast, colorectal, gastric, lung, and prostate carcinomas. MMP-7 is overexpressed in human cancer tissues and proteolytically degrades extracellular matrix of adjacent cells in cancer progression and invasion. It is recognized as a biomarker for various cancers and is distinct in a number of characteristics from the 23 identified MPPs and over expressed in various cancers including stomach, liver, colon, and breast cancers.

Presently, no commercial legumain- and cathepsin-biosensor have been reported, while diagnostic detection of MMP-7 requires the use of conventional fluorogenic proteolytic beacon and enzyme-linked immunosorbent assay (ELISA). There are three main limitations: 1) only one protease can be analyzed in each measurement, 2) a large amount of sample and reagent is necessary, and 3) a workstation in a centralized lab is required. What is needed is an improved method for rapid detection of early stage cancers and "point-of-care" monitoring of treatment response.

SUMMARY OF THE INVENTION

According to one embodiment of the present invention there is provided a nanoelectrode array comprising a substrate having a plurality of carbon nanofibers extending vertically therefrom. The array is capable of detecting the presence of one or more enzymes present within a biological sample. In particular embodiments, the nanoelectrode arrays comprise one or more peptides or peptide residues covalently attached to the exposed distal tips of the carbon nanofibers. When contacted with a sample comprising one or more target enzymes, the enzymes cleave at least some of the peptides or peptide residues, which cause a change in the electrical signal of the array as measured by AC volatammetry.

According to another embodiment of the present invention there is provided an electronic chip comprising a plurality of the nanoelectrode arrays as described herein. In particular embodiments, the electronic chip is useful for detecting specific enzymes, the presence of which are biomarkers of various cancers such as breast, lung and liver cancer, and other diseases such as Alzheimer's disease and various viral infections. Thus, the nanoelectrode arrays and electronic chips comprised of the arrays can be applied for rapid screening tests and monitoring of treatment response. In addition, the electronic chips may comprise a nanoelectrode arrays configured to detect a plurality of different enzymes within a biological sample.

According to still another embodiment of the present invention there is provided a method of detecting an enzyme within a biological sample comprising contacting said biological sample with one or more nanoelectrode arrays as described herein. In a particular embodiment, the method comprises detecting the presence of cancer in an animal by detection of overexpressed proteases. Certain methods according to the present are directed toward an electrochemical method for measuring the activity of proteases using nanoelectrode arrays fabricated with vertically aligned carbon nanofibers. In certain embodiments, a plurality of individually addressed nanoelectrode arrays is provided on an electronic chip. The nanoelectrode arrays contained on the chip may be configured to detect a plurality of different proteases. Upon contact with a biological sample containing one or more target enzymes, the cleavage of a peptide or peptide residue attached to the carbon nanofibers comprising the array results in a change in the redox signal of an organometallic moiety attached to the peptide or peptide residue. This change in redox signal is measured with AC voltammetry.

In yet another embodiment of the present invention there is provided a method of fabricating a nanoelectrode array. In particular, the method of fabricating the nanoelectric array comprises providing an electrically conductive substrate having a plurality of vertically aligned carbon nanofibers attached thereto. The nanofibers comprise a proximal end that is attached to a surface of said substrate and a distal end that is spaced therefrom. The plurality of vertically aligned carbon nanofibers are encapsulated in an insulative material. A portion of the insulative material is then removed so as to expose one or more of the nanofiber distal ends. One or more peptides or peptide residues are attached to one or more of the exposed nanofiber distal ends.

DETAILED DESCRIPTION OF THE PREFERRED EMBODIMENT

Figure 1:
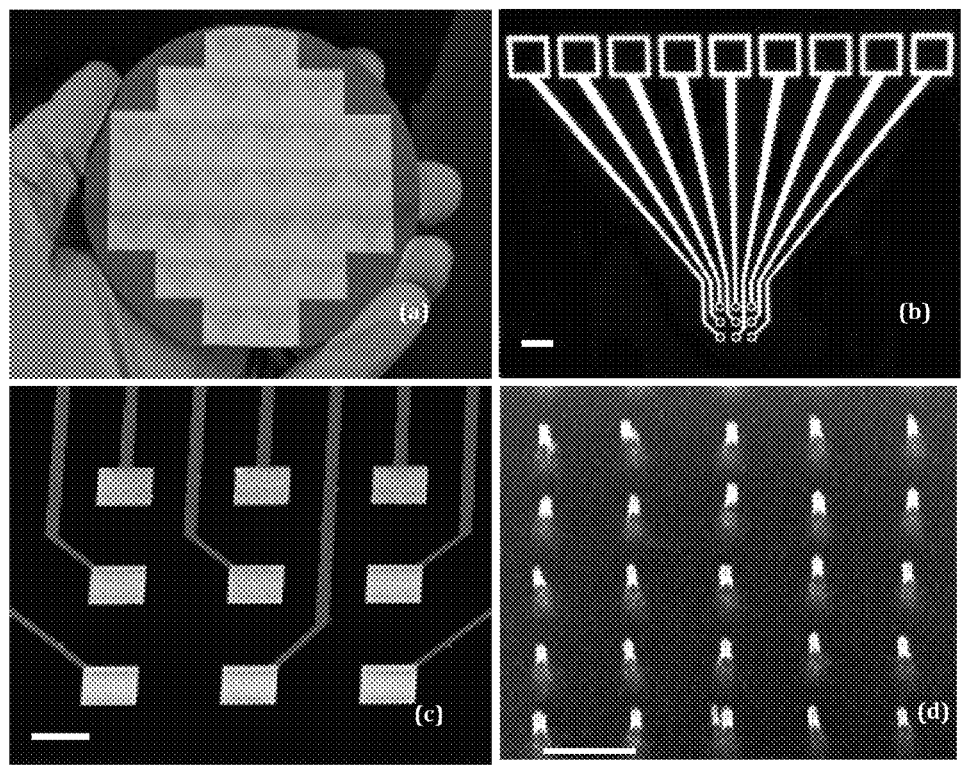
FIG. 1 illustrates multiplex nanoelectrode arrays (NEAs) in accordance with one embodiment of the present invention: (a) is an optical image of 30 dies on a 4" Si wafer, (b) depicts the individually addressed 3×3 microelectrodes on a single die, (c) is a zoom-in view of the active sites of the 3×3 microelectrodes (scale bar=200 nm), and (d) depicts the regular carbon nanofibers (CNFs) at each microelectrode (scale bar=1 μm)

Nanoeletrode arrays (NEAs) with vertically aligned carbon nanofibers (VACNFs, a special type of carbon nanotubes) can be fabricated and are effective in detecting the presence of various enzymes within a fluid sample by recording the proteolysis kinetics of various peptides or peptide residues attached to the carbon nanofibers. In certain embodiments, this electrochemical platform can specifically detect nanomolar concentrations of enzymes, such as legumain, cathepsin B, and MMP-7, within a biological sample with greater than 40 times higher sensitivity than conventional glassy carbon electrodes (GCE). Moreover, in further embodiments, non-specific binding is not a concern and false positive results are minimized by specific proteolytic rates and pattern profiling of each target enzyme (particularly proteases) using a library of enzyme substrates. The NEAs made in accordance with the present invention are useful with established specific biomarkers as a label-free electronic method for rapid profiling of the activities of cancer-related proteases.

Certain embodiments of the present invention provide extremely sensitive label-free electronic detection methods for reliable and rapid profiling of multiple cancer protease activities. These applications are characterized by: (1) increasing detection specificity and reliability using a library of peptide substrates that are tagged with a redox moiety at the electrode surface for specific proteolysis reaction; (2) enhancing detection sensitivity by combining the NEA with alternating current voltammetry (ACV); and (3) functional profiling the cleavage kinetics of redox-tagged peptides which is specific and directly linked to the enzymatic activity. This integrated technology is distinguished from fluorescence techniques which present high false positive rates due to nonspecific binding (particularly in detecting complex mixtures such as cell lysates and serum) and antibody-antigen affinity platforms which do not directly detect enzyme activities. Embodiments of the present invention can be used for initial low-cost cancer screening tests and monitoring treatment responses as a point-of-care system for cancer patients in hospital, army personnel, and even nursing homes.

In certain embodiments, the NEAs are fabricated by growing a plurality of VANCFs on a metallic or metal-coated substrate. In certain embodiments, the substrate comprises an electrically conductive metal such as chromium, titanium, molybdenum, platinum, and gold. In particular embodiments, the metal is coated onto a semi-conductive substrate such as silicon. In these embodiments, the metal coating has an average thickness of between about 25 to about 200 nm, between about 50 to about 150 nm, between about 75 to about 125 nm, or about 100 nm. A thin film of a catalytic material, such as nickel, cobalt and iron, may be applied to the substrate to promote CNF growth. This thin film of catalytic material may have an average thickness of between about 1 to about 50 nm, between about 5 to about 40 nm, between about 10 to about 30 nm, or about 22 nm. In one embodiment, the VANCFs are grown on the substrate using a DC-biased plasma enhanced chemical vapor deposition (PECVD) system. The electric field helps to align the CNFs vertically on the substrate surface.

In certain embodiments, the CNFs, which comprise carbon nanotubes, have an average length of between about 1 to about 10 µm, between about 2 to about 8 µm, between about 4 to about 6 µm, or about 5 µm. The CNFs have average diameters of between about 50 to about 300 nm, between about 75 to about 250 nm, or between about 100 to about 200 nm. The CNFs are separated from each other on the substrate by an average distance of between about 100 to about 600 nm, between about 200 to about 500 nm, or between about 300 to about 400 nm.

Following growth of the VACNFs, an insulative material is deposited on the substrate so as to coat the substrate surface from which the CNFs extend and fully encapsulate each individual CNF. In certain embodiments, the insulative material is a dielectric material such as $SiO_2$, $Si_3N_4$, and $Al_2O_3$, or polymer such as epoxy, poly(methyl 2-methylpropenoate) (PMMA) and poly(p-xylylene) (parylene). The insulative material may be deposited using a chemical vapor deposition (CVD) method from, for example, vapor-phase precursor tetraethylorthosilicate (TEOS), or vacuum vapor deposition for parylene, or solution casting for epoxy.

Next, insulative material is removed so as to expose the tips of one or more of the VACNFs. In one embodiment, this is accomplished by polishing the surface of the insulative material using, for example 0.3 µm alumina slurry, to produce a planar surface. This may be followed by an etching process, such as reactive ion etching (RIE) with a mixture of $CHF_3$ and $O_2$ gases, to selectively etch away a desired amount of insulative material. In certain embodiments, between about 10% to about 70%, between about 20% to about 60%, between about 25% to about 55%, or between about 30% to about 50% of the CNF tips are ultimately exposed based on the length variation among the CNFs. Thus, in certain embodiments, the average spacing between exposed tips is between 500 nm to about 5 µm, between about 750 nm to about 3 µm, or between about 1 to about 2 µm. The average length of exposed CNF tips can be controlled by varying the etch time. However, in certain embodiments, the average length of the exposed tips is between about 50 to about 300 nm, between about 100 to about 250 nm, or between about 125 to about 200 nm.

Peptides or peptide residues are then attached to one or more of the exposed CNF tips. As used herein, it is understood that the term "peptide" includes short chains of amino acid monomers linked by peptide bonds as well as longer chains of amino acid monomers (i.e., "polypeptides"). The peptides or peptide residues may be synthesized according to various reaction schemes, examples of which are discussed in further detail in the Examples. According to certain embodiments of the present invention, peptide or peptide residue selection is determined in large part by the particular target enzyme for detection by the NEA. Particularly, the peptide or peptide residue selected is capable of being cleaved by the target enzyme. In certain embodiments, the peptide or peptide residue comprises between 2 to 15 amino acids, between 3 to 12 amino acids, or between 4 to 10 amino acids.

In certain embodiments, the NEAs are configured to detect the presence of certain enzymes that are overexpressed by cancer-causing cells. Examples of these enzymes include various proteases such as legumain, cathepsin B, and MMP-7. Thus, in particular embodiments of the present invention, the peptide or peptide residue comprises, consists of, or consists essentially of a tetrapeptide Ala-Ala-Asn-Leu (SEQ ID NO:1), which is cleaved by legumain at the carbonyl functional group of the Asn residue, Leu-Arg-Phe-Gly (SEQ ID NO:2), which is cleaved at the carbonyl functional group of the Arg residue, and Pro-Leu-Ser-Leu (SEQ ID NO:3), which is cleaved by MMP-7 at the serine carboxyl functional group.

In certain embodiments of the present invention, a redox moiety that is capable of undergoing a change in oxidation state may be further attached to the free or unbound end of the peptide. The appended redox moiety provides a characteristic faradaic signal that can be separated from the unstable nonFaradaic background and other interfering redox signals. In particular embodiments, the redox moiety is an organometallic moiety, and particularly a metallocene, such as ferrocene or multiple ferrocenes, thus resulting in a ferrocenyl peptide or peptide residue. The increase of number of ferrocene moieties would increase the redox potentials and in turn enhance the detection sensitivity.

In other embodiments, the peptide or peptide residue can be selected to detect the presence of an enzyme in a fluid sample through direct measurement of the impedance change at the electrode surface during by enzymatic phosphorylation/dephosphorylation of the peptide. In this embodiment, a long peptide, such as Biotin-AEEEIY-GEFEAKKKKC (SEQ ID NO:4), which is specific to c-Src kinase, is attached to one or more of the exposed VACNF tips. When a solution containing c-Src kinase and adenosine-5-triphosphate (ATP) is added into the solution, a phosphate group in ATP is transferred to the tyrosine residue in the peptide, referred to as phosphorylation. During this process, a negative charge is added to the peptide, which may be accompanied by a conformational change in the peptide. These affect the packing of peptides on the electrode surface and cause impedance change. Also, the reverse reaction to remove the phosphate group, i.e. dephosphorylation, may occur after replacing the kinase solution with that of protein tyrosine phosphatase 1B (PTP1B). The impedance may change toward the opposite direction.

In certain embodiments, the peptide or peptide residue to attached to the CNFs by a linker molecule. As depicted in FIG. 1, a linker molecule having an amine functional group is covalently attached to the peptide or peptide residue. The peptide is then attached to the CNF tip by forming an amide bond between the —COOH on CNF and —$NH_2$ in the peptide linker. In certain embodiments, the linker molecule is an amino acid residue derived from such as N-Boc-5-aminovaleric acid, in which the Boc protecting group has been removed.

Before the peptides or peptide residues are attached to the CNF tips, the surface of the NEAs may be passivated with a protective moiety, anchored to the $SiO_2$ insulative material in particular, that prevents non-specific adsorption of enzymes, thus eliminating false positive detection of the target enzymes. In certain embodiments, ethylene glycol moieties are covalently anchored to the surface of the NEAs. The molecules attached to the CNF tips are removed by an electrochemical etching process to form clean CNF tips containing abundant carboxylic acid functional groups for peptide functionalization. The passivation of the surrounding insulator surface around the active nanoelectrode tips (<1% of the total surface area) can reduce the loss of enzyme from the solution due to their irreversible nonspecific adsorption onto the non-active chip surface.

In certain embodiments of the present invention, a plurality of NEAs as described herein can be fabricated on a electronic chip, and in particular a silicon chip. In a particular embodiment, the chip may comprise a plurality of non-patterned NEAs with randomly distributed CNF tips. These chips are particularly useful for quick, single tests and can be efficiently manufactured in large quantities. In other embodiments, the chip may comprise a plurality of regularly patterned NEAs produced by nano-lithography, nano-imprinting, or other fabrication methods. These chips are particularly useful for applications requiring high-sensitivity multiplex detection. FIG. 1 illustrates multiplexed nanoelectrode arrays. (a) is an optical image of 30 dies on a 4 inch silicon wafer. (b) illustrates the individually addressed 3×3 micro electrodes on a single die. (c) is a zoom-in view of the active sites of the 3×3 microelectrodes. (d) shows the regular carbon nanofibers at each microelectrode. Regardless of the embodiment, the NEAs contained on the chip can be individually addressed and number into the hundreds.

In certain embodiments, different peptide substrates can be functionalized at different NEAs. Thus, in these embodiments, the chip comprises at least two individually addressed NEAs in which a first peptide or peptide residue is attached to at least one of the carbon nanofibers of one of the NEAs, and a second peptide or peptide residue is attached to at least one of the carbon nanofibers of one other of the NEAs. Thus, the chip comprising the differently functionalized NEAs are operable to detect the presence of at least two different enzymes contained within a biological sample brought into contact therewith.

In certain embodiments, fabrication of chips comprising a plurality of regularly patterned NEAs includes five steps: (1) patterning individually addressed microelectrode pads on the chip using standard UV-lithography; (2) deposition of a thin layer (10 to 30 nm) of catalyst at e-beam patterned regular spots on the microelectrode surface; (3) growth of vertically aligned CNFs at the catalyst sites; (4) encapsulating the device with a insulative material layer, e.g., a $SiO_2$ layer by tetraethoxylsilane using chemical vapor deposition; and (5) chemical mechanical polishing or reactive ion etching to expose the distal ends of the CNFs.

Methods according to the present invention can be used to detect various enzymes present in biological samples, such as blood, serum, urine, saliva, and tissue lysate. In embodiments of the present invention, the biological sample is contacted with one or more NEAs, preferably located on a chip comprising a plurality of NEAs. In certain embodiments of the present invention, enzyme profiling within a sample is based upon a peptide proteolysis mechanism in which the target enzyme cleaves the peptide that is attached to the CNFs thereby resulting in a change in voltage as measured by AC voltammetry due to the removal of the redox moiety (e.g., ferrocene). The presence of the redox moiety on the CNFs gives rise to a particular electrochemical signal. For example, when the redox moiety is ferrocene (Fc), a ferrocenyl peptide, comprising ferrocenium ($Fc^+$), is created, which is attached to the distal end of the CNF. (The proximal end of the CNF is attached to the substrate.) The electron transfer from Fc to the carbon electrode is effective even though they are separated by the peptide and linker molecule. Upon cleavage of the peptides or peptide moieties, the redox moiety is released thereby resulting in a decrease in the AC peak current due to the loss of this moiety. The rate of change is associated with the enzyme specific activity. Proteolytic rates and kinetic profiles from a library of peptide substrates may allow distinctive detection of different enzymes, including cancerous proteases.

It was discovered that maximum peak current appeared at significantly higher frequencies than conventional macroscopic glassy carbon electrodes (GCEs). For example, the AC voltammetry can be performed at frequencies of at least 500 Hz, at least 1200 Hz or at least 1700 Hz. In particular embodiments, the frequency used for the AC voltammetry can be within the range of about 500 to about 3000 Hz, between about 800 to about 2500 Hz, or between 1000 to about 2000 Hz, as compared to 40 Hz for GCEs. In certain embodiments, the amplitude of the AC voltage can be within the range of about 1 to about 400 mV, between about 50 to about 300 mV, or between about 100 to about 200 mV. These characteristics lead to greater than 40 times higher sensitivity and much faster measuring speeds as compared to GCEs. In certain embodiments, the time to complete an ACV measurement can be reduced to less than 1 minute, less than 30 seconds, less than 5 seconds, or less than 1 second. In particular embodiments, optimization of frequency and amplitude can result in completion of ACV measurements within about 0.01 to about 60 seconds, about 0.1 to about 30 seconds, or about 0.2 to about 5 seconds.

The enzymatic reaction involves two parts: an enzyme and a corresponding peptide substrate (with a specific sequence of amino acids). An individual enzyme reacts with its specific substrate(s) in a greatest rate (or catalytic efficiency). In certain embodiments, the nanoelectronic chip is configured to simultaneously detect one or more overexpressed proteases in cancers, such as legumain, cathepsin B, and MMP-7, and use a non-cancer related protease, such as chymotrypsin, as a reference. As illustrated in FIGS. 2a and b, the specially designed peptide substrates specific for each protease comprise a redox tag (dot with a tail in FIG. 2b) that give rise to an electrochemical signal. Each specific substrate is covalently attached to the carbon nanofibers (CNFs) at one NEA pad. When a specific enzyme in a mixed sample solution selectively binds to its specific substrate, a proteolytic reaction occurs at the electrode surface, leading to the decrease of the electrochemical signal due to the loss of the organometallic moiety from the electrode surface. The signal over time may be recorded simultaneously at each individually addressed NEAs using, for example, an integrated multiplex potentiostat with a touchscreen to display individual proteolytic reaction kinetics (or rates) and specificity patterns.

The exponential decay in the electrochemical signal can be analyzed with the heterogeneous Michaelis-Menten model, described in greater detail in the Examples, to derive the value of $(k_{cat}/K_M)[E]$. The fundamental specificity constant (or catalytic efficiency) $k_{cat}/K_M$ (with $K_M=(k_{-1}+k_{cat})/k_1$)) can be first determined using known concentration of the proteases for calibration. Then the concentration of the specific proteases [E] in the unknown sample can readily be determined with its kinetic data.

Embodiments of the present invention are particularly suited for application in a portable electronic system for simultaneous electrochemical signal detection by a plurality of independent channels connected to a chip comprising a plurality of NEAs. The VACNF NEA chip can be fabricated as a disposable cartridge with a total reaction volume of about 200 µL-about 500 µL. A common reference electrode and a common counter electrode may also be used, while each working electrode, i.e. a VACNF-NEA on each microelectrode pad will be independently addressed based on phase-sensitive ACV. The sensitivity should be sufficient to detect ~0.1 nA AC current generated from the electrochemical signal. The electronic system may be reconfigured from a commercial chip (for example, LMP9100 of National Semiconductor or Atmel XMEGA microcontroller) and integrated with a specially designed circuit board into a multi-channel potentiostat. A touchscreen liquid crystal display (similar to a smartphone or tablet device) may be incorporated for display as a part of a standalone handheld device.

In certain embodiments, a data acquisition and a user interface with touchscreen technique may be developed using, for example, C# (Micro Visual Studio). Once the data is collected, the data analysis program performs a real-time analysis, including analyzing the incoming signals and displaying the enzymatic kinetics, reaction pattern based on the location of the signal source (i.e., pre-assigned specific NEA position in the array) and the completed data. The data analysis process includes subtracting the linear background and extracting the peak AC current. The value of extracted AC peak current is plotted vs. time (for ~15 to 60 minutes) as a kinetic curve. The program then initiates an automatic data fitting process using the heterogeneous Michaelis-Menten model described below. The value of the specificity constant $k_{cat}/K_M$ of each specific enzyme is pre-input according to data contained within a known library. As a result, the enzyme concentration (or activity) can be derived and the final results can be obtained in about 30 to 60 minutes.

EXAMPLES

The following examples describe exemplary nanoelectrode arrays and methods of using the same to detect the presence of certain enzymes present within a biological sample in accordance with the present invention. It is to be understood, however, that these examples are provided by way of illustration and nothing therein should be taken as a limitation upon the overall scope of the invention.

Example 1

In this Example, two types of enzymatic biosensors were prepared and tested: (1) a redox labeled ACV biosensor for protease (legumain) detection, and (2) a label-free REIS biosensor for kinase/phosphatase detection. These enzymes are critical in regulating cell behaviors, whose overexpression in human body is known to associate with various cancers. These electrochemical methods, particularly with the enhancement by NEAs, have the potential as multiplex portable techniques for rapid diagnosis or treatment monitoring of cancer patients. These two enzymatic sensors share similar fabrication techniques, but differ in the detection mechanism due to the nature of the reactions.

Figure 2:
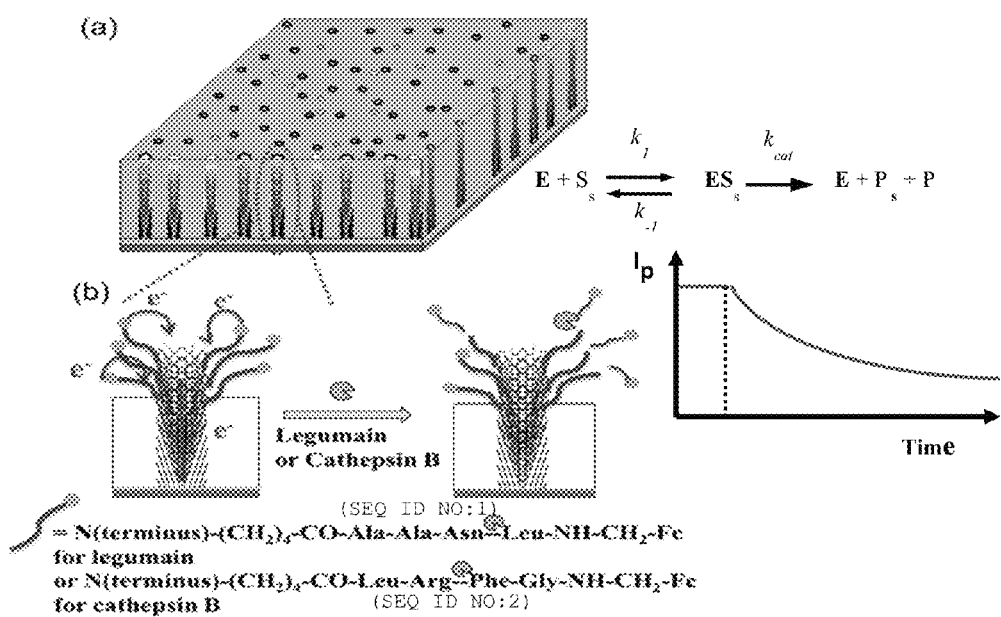
FIG. 2 is a schematic illustration of the principles of enzymatic detection at each NEA, (a) illustrates the vertically aligned carbon nanofibers (VACNFs) at the microelectrode pads embedded in an insulative material leaving only the tip exposes, (b) illustrates the tagged peptides attached at the CNF tips that provide an electrochemical signal, the proteolytic kinetics of the peptide is recorded by measuring the electrochemical signal versus time and analyzed with a heterogeneous Michaelis-Menten model.

In the protease study, a tetrapeptide $H_2N-(CH_2)_4-CO$-(SEQ ID NO:1)-NH—$CH_2$-Fc is covalently attached to the exposed tip of a VACNF NEA as shown in FIG. 2. Fc provides reliable redox signals at 0.25 V vs. Ag/AgCl (3M KCl) in ACV measurements. As shown in later sections, the unique structure of VACNF NEA enables the enhanced ACV signal at over 1750 Hz AC frequency. Upon being supplied with legumain (a cancer related protease), the peptide is cleaved at the site between Asn and Leu. As a result, the Fc moiety is released from the electrode surface into bulk solution, causing the redox signal to decrease. The kinetic of the enzymatic reaction at the electrode surface can be monitored by continuously repeated ACV measurements. The advantage of this method is that the Fc label provides a characteristic redox signal which can be easily separated from the nonFaradaic background and other redox signals. However, the mechanism becomes complicated for enzymes requiring much longer peptide sequences for specific recognition. The Fc signal involves electron transfer between Fc molecule and the electrode surface, which is highly sensitive to the Fc surface distance. This may vary in a large range depending on the molecular packing of the long peptides on the electrode surface.

Figure 3:
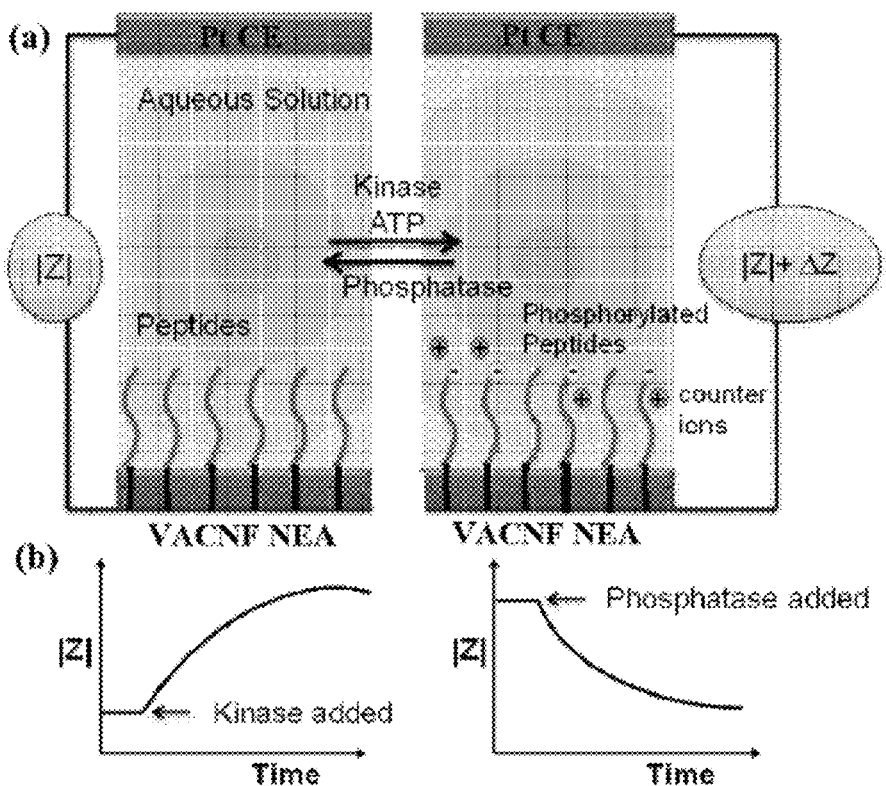
FIG. 3 is a schematic of the principles of label-free detection of enzymatic activities of a pair of kinase and phosphatase by real-time electrochemical impedance spectroscopy (REIS), (a) illustrates the reversible phosphorylation and dephosphorylation of surface attached peptide substrates catalyzed by kinase and phosphatase, respectively, and (b) illustrates an REIS curve (|Z| vs. time) during the enzymatic phosphorylation and dephosphorylation reactions.

In the kinase/phosphatase study, a label-free REIS method was employed which directly measures the impedance change at the electrode surface during enzymatic phosphorylation/dephosphorylation, as shown in FIG. 3. A long peptide substrate (Biotin-AEEEIYGEFEAKKKKC (SEQ ID NO:4)) which is specific to c-Src kinase is attached to the exposed CNF tip. When a solution containing c-Src kinase and adenosine-5-triphosphate (ATP) is added into the solution, a phosphate group in ATP is transferred to the tyrosine residue in the peptide, referred as phosphorylation. During this process, a negative charge is added to the peptide, which may be accompanied by a conformational change in the peptide. These effects are expected to affect the packing of peptides on the electrode surface and cause impedance change. On the other hand, the reverse reaction to remove the phosphate group, i.e. dephosphorylation, could happen after replacing the kinase solution with that of protein tyrosine phosphatase 1B (PTP1B). The impedance may change toward the opposite direction. It is possible to monitor the phosphorylation/dephosphorylation kinetics with REIS measurements.

Heterogeneous Enzymatic Kinetics

The kinetics of the above two heterogeneous enzymatic reactions are generally explained with the modified Michaelis-Menten model.

$$E + S_s \underset{k_{-1}}{\overset{k_1}{\rightleftharpoons}} ES_s \xrightarrow{k_{cat}} E + P_s + P. \quad (1)$$

where E, $S_s$, $ES_s$, P and $P_s$ represent the enzyme, the surface-bound peptide substrate, the enzyme-substrate complex on the electrode surface, the surface-attached product, and the product released to solution, respectively. The reaction rate can be defined as

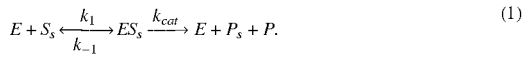

$$v = -\frac{d\Gamma_{Ss}}{dt} = \frac{d\Gamma_{Ps}}{dt} = \frac{k_{cat}[E_0] \times \Gamma_{Ss}}{K_m + [E_0]}, \quad (2)$$

where $k_{cat}$ is the dissociation rate constant, $K_m = (k_{cat} + k_{-1})/k_1$ is the Michaelis-Menten constant, and $\Gamma_{Ss}$ and $\Gamma_{Ps}$ represent the surface densities of original and reacted peptide substrates, respectively. At low enzyme concentrations where $[E_0] \ll K_m$, an approximate relationship can be obtained as $$\upsilon = -\frac{d\Gamma_{Ss}}{dt} = \frac{d\Gamma_{Ps}}{dt} = \frac{k_{cat}}{K_m}[E_0] \times \Gamma_{Ss}. \quad (3)$$

The reaction rate v (or $-d\Gamma_{Ss}/dt$) is a time-dependent quantity proportional to the change in electrochemical signals (dS/dt), where S is the kinetic electrochemical signal corresponding to the peak current $i_p$ in ACV measurements for protease and the normalized impedance $|Z|/|Z_0|$ in REIS measurements for kinase/phosphatase, respectively. As a result the slope of (dS/dt) versus the time-dependent $\Gamma_{Ss}$ will be equal to $(k_{cat}/K_m)[E_0]$, namely $$-\frac{d\Gamma_{Ss}/dt}{\Gamma_{Ss}} = -\frac{dS/dt}{S} = \frac{k_{cat}}{K_m}[E_0]. \quad (4)$$

Thus, by rearranging the kinetic electrochemical data, the value of "specificity constant" $k_{cat}/K_m$ can be derived which is commonly used to represent the catalytic efficiency of enzymes. This algorithm is applied onto two types of electrochemical measurements below.

Materials

Figure 4:
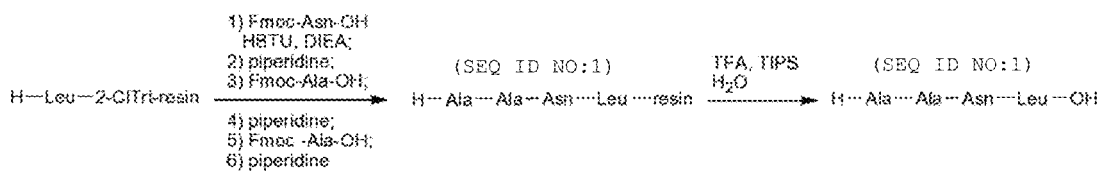
FIG. 4 illustrates the synthesis of $H_2N—(CH_2)_4CO$-(SEQ ID NO:1)-$NHCH_2$-Fc.
Figure 4:
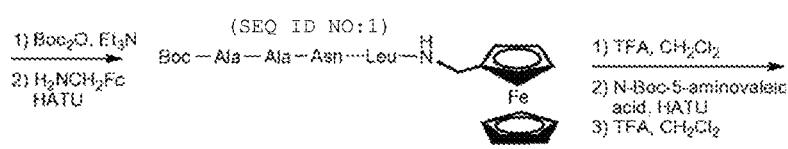
Figure 4:
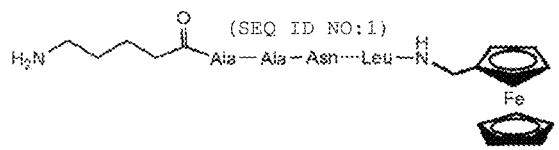

Ferrocene-labeled tetrapeptide for legumain cleavage (i.e., $H_2N—(CH_2)4-CO-(SEQ\ ID\ NO:1)-NH—CH_2-Fc$) was synthesized following the steps in FIG. 4. In brief, H-Leu-2-ClTrt-resin (from Peptide International Inc., Louisville, Ky.) was converted to H-Ala-Ala-Asn-Leu (SEQ ID NO:1) resin from a microwave peptide synthesizer (CEM Inc.) by the sequence: (1) coupling with Fmoc-Asn-OH, O-(benzotriazol-1-yl)-N,N,N',N'-tetramethyluronium hexafluorophosphate (HBTU), and diisopropylethylamine in DMF; (2) removal of the Fmoc protecting group with 20% piperidine in DMF; and (3) similarly, coupling with Fmoc-Ala-OH and removal of Fmoc twice using the same reagents as described above. H-Ala-Ala-Asn-Leu (SEQ ID NO:1) resin was hydrolyzed with trifluoroacetic acid (TFA), triisopropylsilane (TIPS), and water (95:15:25) to give H-(SEQ ID NO:1)-OH, which upon protection of the amino function with di-t-butyl dicarbonate ($Boc_2O$) followed by the coupling with aminomethylferrocene and 2-(7-aza-1H-benzotriazole-1-yl)-1,1,3,3-tetramethyluronium hexafluorophosphate (HATU) afforded Boc-(SEQ ID NO:1)-$NHCH_2Fc$. Deprotection of the aforementioned tetrapeptide ferrocene with 10% TFA in dichloromethane at 25° C. for 30 min. followed by condensation with N-Boc-5-aminovaleric acid and HATU in DMF, and removal of the Boc protecting group with 10% TFA in dichloromethane furnished $H_2N—(CH_2)_4$-CO-(SEQ ID NO:1)-$NHCH_2$-Fc.

Recombinant human legumain/asparaginyl endopeptidase (molecular weight 49 kDa) was obtained from R&D Systems Inc. (Minneapolis, Minn.). Before used for enzymatic reactions, legumain was activated in an activation buffer comprising 50 mM $CH_3COONa$ (pH 4.0, adjusted by adding acetic acid) and 100 mM NaCl. Peptide substrate for c-Src kinase (Biotin-AEEEIYGEFEAKKKKC (SEQ ID NO:4)) was synthesized by AnaSpec, Inc. (Fremont, Calif.). Active c-Src kinase protein (N-terminal 6His-tagged recombinant human c-Src, molecular weight 61.7 kDa) was purchased from Milipore (Billerica, Mass.). PTP1B (residues 1-322, molecular weight 37.4 kDa) was purchased from Enzo Life Sciences, Inc. (Plymouth Meeting, Pa.).

Fabrication of VACNF NEAs

The NEAs were fabricated by encapsulating VACNFs in $SiO_2$ matrix on a silicon chip using the method described in J. Li et al., "Inlaid multi-walled carbon nanotube nanoelectrode arrays for electroanalysis," Electroanalysis 17(1), 15-27 (2005) and J. Li et al., "Carbon Nanotube Nanoelectrode Array for Ultrasensitive DNA Detection," Nano Letters 3(5), 597-602 (2003), both of which are incorporated by reference herein in their entireties. Briefly, VACNFs of an average length of ~5 μm were grown on ~100 nm Cr coated Si substrate using a DC-biased plasma enhanced chemical vapor deposition (PECVD). A thin nickel film of 22 nm was used as the catalyst to promote CNF growth. The electric field helped to align the CNF vertically on the substrate surface. Dielectric $SiO_2$ was deposited using chemical vapor deposition (CVD) from vapor-phase precursor tetraethylorthosilicate (TEOS) to fully encapsulate the bottom Cr metal contact layer and each individual CNFs. Mechanical polishing was applied using 0.3 μm alumina slurry to produce a flat surface. Reactive ion etching (RIE) with a mixture of $CHF_3$ and $O_2$ gases was then performed to selectively etch away desired amount of $SiO2$ and expose some of the CNF tips. A typical VACNF NEA for electrochemical measurements comprises randomly distributed CNF tips with an average CNF diameter of 100-200 nm and an average spacing over ~1 μm (corresponding to a density of ~1-10×$10^6$ CNFs/$cm^2$). CNF tips of an average length of ~50-300 nm were exposed at the $SiO_2$ surface, which can be controlled by varying the RIE time to selectively remove $SiO_2$.

Electrode Pre-Conditioning

Before each use, VACNF NEAs were further polished with 0.05 μm γ-alumina slurry (Buehler) on napless polishing cloth for 5-15 min, followed by rinsing with deionized water. The VACNF NEAs were then electrochemically activated by etching in 1.0M NaOH solution using four cycles of CV in a potential range of –0.10 V to 1.20 V (vs. Ag/AgCl (3M KCl)) at a scan rate of 50 mV $s^{-1}$.

Passivation of the VACNF NEA Chip

To reduce nonspecific adsorption, the $SiO_2$ surface of VACNF NEAs was first passivated with protective moieties containing ethylene glycol. The chip was immersed in an 8 g/L solution of (3-aminopropyl)triethoxysilane (APTES) in ethanol for 20 min to produce a primary amine derivatized surface. The chip was treated with 50 μL solution of 0.1 mM of 2-[2-(2-methoxyethoxy)ethoxy]acetic acid, 100 g/L of 3-(ethyliminomethyleneamino)-N,N-dimethyl-propan-1-amine (EDC), and 50 g/L of 1-hydroxy-2,5-pyrrolidinedione (sulfo-NHS), and incubated at room temperature for 2 hours. The carboxylic acid group of 2-[2-(2-methoxyethoxy) ethoxy]acetic acid formed an amide bond with the amino function on the chip surface, leaving ethylene glycol moiety covering the surface. The molecules attached to the CNF tips were then removed by electrochemical etching at 1.2 V (vs. Ag/AgCl (3M KCl)) for 20 sec. in 1.0M NaOH solution. This process regenerated clean CNF tips that contain abundant carboxylic acid functional groups.

Functionalization of the VACNF NEA Chip

For protease analysis, the tetrapeptide $H_2N—(CH_2)_4$—CO-(SEQ ID NO:1)-$NHCH_2$-Fc was covalently linked to the VACNF NEA by forming amide bond facilitated by EDC and sulfo-NHS. In order to stabilize the electronic signal, the electrode surface was reacted with 6-amino-1-hexanol to fill the remaining —COOH sites. For kinase/phosphatase analysis, the c-Src kinase peptide substrate (Biotin-AEEEIY- GEFEAKKKKC (SEQ ID NO:4)) was conjugated to the carboxylic acid group at the CNF surface through a hexanediamine and a maleimide which crosslinks with the cysteine. The coupling of the peptides to CNFs was verified with SEM to inspect the binding of streptavidin-derivatized latex beads (50 nm in diameter) to the biotin at the distal end of the peptide substrate.

Validation of the Enzyme Activities with Other Biochemical Methods

All enzymes were first validated with established biochemical methods before electrochemical experiments. The legumain activity was measured with a kinetic fluorescence assay using a commercial substrate Z-Ala-Ala-Asn-AMC (Bachem, Torrance, Calif.) which gave strong fluorescence after cleavage at the site between asparagine and AMC dye. Src kinase and PTP1B phosphatase were inspected with a protein tyrosine kinase kit based on enzyme-linked immunosorbent assay (ELISA) (Sigma-Aldrich, Saint Louis, Mo.).

Electrochemical Measurements

The electrochemical measurements were performed in a TEFLON cell with a total volume of 250 μL for legumain experiments and 120 μL for kinase/phosphatase experiments. The cell was sealed against a VACNF NEA chip with a 3-mm i.d. O-ring in a three-electrode configuration with the VACNF NEA as the working electrode, an Ag/AgCl (3M KCl) reference electrode and a coiled Pt wire as the counter electrode. ACV measurements for protease analysis were carried out with a model 440A electrochemical analyzer (CH Instruments, Austin, Tex., USA). The electrolyte solution consisted of 50 mM MES pH 5.0) and 250 mM NaCl. The average AC current was measured as the potential was swept from −0.05 to +0.65 V at 10 mV/s scan rate using a staircase waveform. The REIS experiments for kinase and phosphatase analysis were controlled by a potentiostat (PARSTAT 2273, Princeton Applied Research Corporation) at the open circuit potential with a 20 mV (rms) AC voltage at fixed frequency (1000 Hz). REIS for phosphorylation was carried out in tyrosine kinase buffer (500 mM HEPES, pH 7.4, 200 mM $MgCl_2$, 1 mM $MnCl_2$, and 2 mM $Na_3VO_4$) purchased from Sigma-Aldrich (Saint Louis, Mo.) and that for dephosphorylation was carried out in a phosphatase buffer (50 mM HEPES, pH 7.2, 1 mM EDTA, 1 mM DTT) that was prepared in house. This buffer was modified from the commercial phosphatase buffer by removing one of the composition (0.05% NP-40), which is a surfactant causing bubble formation and inducing large electrochemical noises. Other parameters were varied in specific experiments and are specified as the results presented below.

ACV Electrochemical Biosensor for Protease

ACV uses a sinusoidal AC voltage superimposed on a DC potential ramp for voltammetric measurements. It has advantages over commonly used DC-based CV, particularly for biosensors, due to the ability to amplify the electrochemical signal of small quantity of redox tags by shuffling the electron between the redox tag and the electrode many times. In general, the signal increases with AC frequency at low frequencies but is saturated and then decreases at higher frequencies. Using VACNF NEAs, the optimum frequency for Fc through a short $NH_2CH_2$-linker was found to be 40 times higher than macroscopic glassy carbon electrode (GCE). Similar phenomena were also observed with Fc attached to the electrode surface through a tetrapeptide and linker groups, i.e. $H_2N$—$(CH_2)_4$—CO-(SEQ ID NO:1) $NHCH_2$-Fc. A peak current was observed at ~0.2 V vs. Ag/AgCl (3M KCl) for both macro-GCEs and VACNF NEAs.

The amplitude of the peak current density ($i_p$) in the ACVs with macro-GCE increased from ~$1.0 \times 10^{-7}$ A/mm² at 10 Hz to $2.0 \times 10^{-7}$ A/mm² at 40 Hz but then drop to zero at 1500 Hz. At the meantime, the background signal steadily increased from ~$4.7 \times 10^{-7}$, to $1.8 \times 10^{-6}$ and $2.8 \times 10^{-6}$ A/mm², respectively. In contrast, although the $i_p$ of ACV with VACNF NEAs was not measurable at 10 Hz and 40 Hz, it rose clearly above the background at 1500 Hz. VACNF NEAs allowed the Fc signal to be detected at high frequency. Generally, the electrochemical signal is very sensitive to Fc-surface distance since electron transfer rate decays exponentially from the surface and is only at a meaningful level within 2 nm distance. Here the electron transfer on both GCEs and VACNF NEAs was not affected by the tetrapeptide and the linker, likely because the chain was short and might be folded back to bring Fc closer to the CNF surface.

A difference in frequency dependence between a GCE and a VACNF NEA was observed. The optimum frequency which gave the maximum $i_p$ was 40 Hz for the GCE but 1750 Hz for the VACNF NEA. The latter value is ~44 times of the former. Higher frequency at VACNF NEA afforded a larger ACV signal (i.e., $i_p$) and shorter time for the ACV measurements. As a result the kinetic of enzymatic cleavage can be followed with continuously repeated ACV measurements.

The change in peak current ($i_{p,acv}$) during continuously repeated ACV measurements with Fc-linked tetrapeptide immobilized on a VACNF NEA was measured. The initial signal was quite stable, with only slow drifting. At ~20 minutes, 10 μL of 983 ng/μL (201 μM) legumain in the activation buffer was added to the electrochemical cell. Due to the change in electrolyte composition, the ACV peak current jumped up. Interestingly, an exponential decay was observed afterward. The insets further illustrate the representative full ACV curves corresponding to three points in the initial stage, right after adding legumain, and about 55 minutes after adding legumain, respectively. Two control experiments were carried out to confirm that the exponential decay in $i_{p,acv}$ was attributed to the kinetics of enzymatic cleavage to the peptide. First, 11 μL of blank activation buffer (i.e., 50 mM $CH_3COONa$ (pH=4.0, adjusted by adding acetic acid) and 100 mM NaCl) was added into the electrochemical cell prefilled with 250 μL of electrolyte (50 mM MES (pH 5.0) and 250 mM NaCl). The disturbance to the ACV signal was negligible in this process. Second, 11 μL of activation buffer containing deactivated legumain (which was confirmed with the fluorescence assay) was added into the electrochemical cell in the similar way as above. This caused a step-like jump in $i_{p,acv}$ which remained flat afterward without showing the characteristic exponential decay. It seems that legumain (whether in active form or not) tends to interact with peptide and causes disturbance to the Fc-surface distance, leading to the step-like jump in $i_{p,acv}$ while the activation buffer (though has different composite from the electrolyte) does not affect Fc signal.

To further analyze the kinetic enzymatic process, the peak current in ACV was converted into the quantity of surface adsorbed Fc (i.e., $\Gamma_{surf}$) based on $$i_{p,ac} = \left(\frac{2}{\pi}\right)\left(\frac{F^2}{4RT}\right)\Gamma_{surf}(2\pi f)V_0,$$

where the AC frequency f was 1750 Hz and the amplitude of the AC voltage $V_0$ was 150 mV. Although the $\Gamma_{surf}$ value derived with equation above is known to deviate from that obtained with other methods (particularly with ACV using high frequencies), the linear relationship between $i_p$, and $\Gamma_{surf}$ remains true. The uncertain proportional coefficient will be cancelled in later steps and does not affect the final results. The kinetic data can be fit with an exponential decay superimposed on a linear curve corresponding to the slow baseline drift. The time constant is 1076 s (~18 min.), indicating that the reaction is quite slow. It normally took 1 hour to complete the kinetic measurement. This was found to be limited by the low enzymatic activity of legumain. With ACV measurements, it was still possible to extract the faradaic signal of Fc from the varying background even in such slow reactions. The measurements would be much more reliable in detecting other proteases with higher activities.

From the fitting equation, the reaction rate v, at different $\Gamma_{surf}$ can be calculated. The results appeared to be a linear curve in the high $\Gamma_{surf}$ region. As mentioned earlier, both $v_i$, and $\Gamma_{surf}$ are proportional to $i_p$. The slope of $v_i$ vs. $\Gamma_{surf}$, however, is independent of the exact proportional coefficient since it presented in both $v_i$ and $\Gamma_{surf}$ and is cancelled. Thus it was possible to derive the exact slope without affected by the ACV experimental conditions. The plot of reaction rate ($v_i$) versus the quantity of surface adsorbed Fc ($\Gamma_{surf}$) during the enzymatic reaction gives a slope of $6.32 \times 10^{-4}$ s$^{-1}$, which equals to $(k_{cat}/K_m)[E_0]$ as described in the Michaelis-Menten model. With $[E_0]$=773 nM, the value of the "specificity constant" $k_{cat}/K_m$ can be calculated as $8.2 \times 10^{-3}$ M$^{-1}$ s$^{-1}$. This value is close to the value of $4.1 \times 10^{-3}$ M$^{-1}$ s$^{-1}$ derived from the fluorescence assay and the specifications provided by the vendor.

Label-Free REIS Electrochemical Biosensors for Kinase/Phosphatase

In the above ACV method, there are two drawbacks: (1) the requirement of redox labeling; and (2) the rather long time (~1 min) to complete each ACV measurement which limits the sampling rate for the kinetic measurements. For fast enzymatic reactions, it is desirable to use a label-free fast electrochemical method. This can be achieved with REIS. In this section, this method is used for studying the reversible phosphorylation/dephosphorylation kinetics catalyzed by kinase/phosphatase.

A long peptide substrate (Biotin-AEEEIYGEFEAKK-KKC (SEQ ID NO:4)) which is specific to c-Src kinase was attached to the exposed tip in a VACNF NEA. Phosphorylation would happen after adding c-Src kinase mixed with ATP. The fully phosphorylated peptides can then be converted back to the original form by dephosphorylation with phosphatase PTP1B. The phosphorylated peptide has a negative charge brought by the phosphate group. Electrochemical impedance is in principle sensitive to the surface charge density or the peptide packing induced by the variation of charge density at the surface. In this REIS study, the electrochemical impedance is monitored at 1000 Hz AC frequency. As a result, fast reaction kinetics can be observed with a temporal resolution of tens of milliseconds.

The REIS upon adding 20 μL c-Src kinase or PTP1B phosphatase into 90 μL of corresponding buffer solutions was determined. Only a small change (<0.5%) in the total impedance value |Z| was observed with 5.9 nM of c-Src kinase. The change was slow, unreliable, and superimposed on a step function due to disturbance to the solution. The peptide at the VACNF NEA was fully phosphorylated with 1-hour further incubation in c-Src kinase solution. The solution was then replaced with 90 μL of phosphatase buffer. The dephosphorylation reaction was monitored with REIS. A stable |Z| value at ~18,180Ω was observed at the beginning, which is much higher than that in kinase buffer mainly due to the difference in buffer composition. A sharp decrease in |Z| by ~1,150Ω (~6.3%) was observed over the ~100 s period after adding 2.4 nM PTP1B. These results indicated that the peptide attached to the VACNF NEA could indeed be reversibly phosphorylated and dephosphorylated by switching the enzymes and corresponding buffers. The impedance change corresponding to the dephosphorylation by PTP1B was considerably larger than that of phosphorylation by c-Src kinase. This was due to the difference in the enzyme activities. It is known that the "specificity constant" $k_{cat}/K_m$ is $1.1 \times 10^6$ M$^{-1}$ s$^{-1}$ for human PTP and $2.9 \times 10^7$ M$^{-1}$ s$^{-1}$ for rat PTP1 phosphatases but is much lower for c-Src kinase, ranging from $2.4 \times 10^3$ to $2.5 \times 10^4$ M$^{-1}$ s$^{-1}$. The specificity constant of legumain is comparable with c-Src kinase, thus the reaction was also very slow. But it was measurable with ACV since the redox signal in ACV was specific and was able to be extracted from the varying nonspecific background. This was not possible with REIS in the slow reaction.

The fast kinetics and significant impedance change during dephosphorylation by PTP1B made it possible for quantitative analysis of the enzyme activity based on the REIS results. The algorithm described above can be applied by replacing the kinetic electrochemical signal S with the normalized REIS quantity $|Z|/|Z_0|$. The raw REIS data after adding PTP1B was extracted and calculated in three steps: (1) a linear baseline drift (almost a constant at ~17,000Ω) was subtracted, (2) the subtracted |Z| value was normalized to $|Z_0|$, the value right before adding PTP1B, and (3) the time at PTP1B addition was reset to zero. The modified curve was then fit with an exponential decay $$|Z|/|Z_0|=0.944\exp(-t/19.1)$$

The value $-d(|Z|/|Z_0|)/dt$ represents the reaction rate, which can be calculated from the exponential fitting function above and then plotted vs. $|Z|/|Z_0|$. This curve can be fit with a straight line with a slope of 0.0522 s$^{-1}$ which equals to $(k_{cat}/K_m)[E_0]$ as described in Equation (4) above. Since it is known $[E_0]$=2.4 nM, the value of $k_{cat}/K_m$ can then be derived as $2.2 \times 10^7$ M$^{-1}$ s$^{-1}$.

It is noteworthy that, although the absolute impedance value |Z| varied in a large range on different NEA chips (from ~11,000Ω to ~18,200Ω), the decay time constants derived from the normalized data (i.e., $|Z|/|Z_0|$ vs. time) are very similar for the same PTP1B concentration. The time constant is the most critical quantity related to the enzyme activity. The value of the time constant for PTP1B in the exponential function above is only 19.1 s, more than 50 times smaller than the 1076 s time constant for legumain. As a result, the measurement can be completed in ~2 min. for (phosphatase PTP1B) instead of 1 hour for legumain. This makes it easy to avoid the slow nonspecific baseline drift, the major limitation of REIS technique. Therefore reliable REIS measurements were obtainable with enzymes of high $k_{cat}/K_m$ values.

In order to rigorously determine the specificity constant $k_{cat}/K_m$, the dephosphorylation reaction was investigated at two lower PTP1B concentrations, 1.8 nM and 1.2 nM, respectively. The representative kinetic curves of $-d(|Z|/|Z_0|)/dt$ vs. $(|Z|/|Z_0|)$ at all three PTP1B concentrations were prepared. The slopes of $-d(|Z|/|Z_0|)/dt$ vs. $|Z|/|Z_0|$ derived from 7 data sets at three PTP1B concentrations shows a linear relationship with the PTP1B concentration. All data points fall on a straight line passing through the origin. The derived specificity constants $k_{cat}/K_m$ are very close to each other with an average value of $2.1 \times 10^7$ M$^{-1}$ s$^{-1}$ and a standard deviation of $1.0 \times 10^6$ $M^{-1}$ $s^{-1}$. This value falls in the range between $1.1 \times 10^6$ and $2.9 \times 10^{-1}$ $M^{-1}$ $s^{-1}$ reported in literature. It is quite convincing that the electrochemical detection by REIS is a valid method for quantitative analyses of PTP1B activity.

In summary, VACNF NEAs can be used for profiling enzyme activities through monitoring the change in electrochemical signals induced by enzymatic reactions of the peptides attached to the CNF tip. The kinetic process can be analyzed with a heterogeneous Michaelis-Menten model to derive the "specificity constant" $k_{cat}/K_m$. In analyzing protease legumain, a simple tetrapeptide with a redox tag (i.e., ferrocene) can provide a characteristic peak current in AC voltammetiy, giving the "specificity constant" $k_{cat}/K_m$ as $8.2 \times 10^3$ $M^{-1}$ $s^{-1}$. Real-time electrochemical impedance spectroscopy (REIS) method can be used for fast label-free detection of phosphorylation by c-Src tyrosine kinase and dephosphorylation by protein tyrosine phosphatase 1B (PTP1B). These two processes were found to be reversible with the impedance change toward the opposite directions. Due to the low $k_{cat}/K_m$ value of c-Src tyrosine kinase, the impedance change measured by REIS during phosphorylation was slow and unreliable. In contrast, the much more active phosphatase PTP1B induced well-defined REIS curve showing a characteristic exponential decay. The decay time constant can be reliably derived with exponential fitting, which appeared to depend on the PTP1B concentration but was not affected by REIS conditions and electrode variation. The derived specificity constants $k_{cat}/K_m$ is about $(2.1 \pm 0.1) \times 10^7$ $M^{-1}$ $s^{-1}$, about three orders of magnitude higher than legumain and c-Src tyrosine kinase. All these enzymatic constants are consistent with literature. By tailoring these two methods, enzymes with the specific constant in a wide range could be measured. These VACNF NEA based electrochemical enzymatic biosensors can be potentially developed into portable multiplex electronic devices for rapid cancer diagnosis and treatment monitoring.

Example 2

In this example, the proteolytic activity of a cancer-related enzyme cathep sin B is measured with alternating current voltammetry (ACV) using ferrocene (Fc) labeled tetrapeptides attached to nanoelectrode arrays (NEAs) fabricated with vertically aligned carbon nanofibers (VACNFs).

Materials and Methods

The electrochemical measurements were conducted with an electrochemical analyzer (Model 440A, CH Instruments, Austin, Tex.). Fluorescence assay was performed on GloMax-Multi+Microplate Multimode Reader (Promega, Madison, Wis.) with black polystyrene 96 well plates obtained from Whatman (Picataway, N.J.). 3-Aminopropyl-triethoxysilane (APTES), 2-(2-methoxyethoxy)ethoxyacetic acid, 1-ethyl-3-(3-dimethylaminopropyl)carbodiimide hydrochloride (EDC), 1-hydroxy-2,5-dioxopyrrolidine-3-sulfonic acid sodium salt (sulfo-NHS), sodium hydroxide, and 6-amino-1-hexanol were purchased from Sigma-Aldrich (Saint Louis, Mo.). 2-(4-Morpholino)ethane sulfonic acid (MES) and dithiothreitol (DTT) were purchased from Thermo Fisher Scientific (Fair Lawn, N.J.). Purified recombinant human cathepsin B (molecular weight of 29 kDa) was acquired from R&D Systems Inc. (Minneapolis, Minn.). Human breast whole tissue lysate (adult normal) with the stock concentration of 4.9 mgmL$^{-1}$ was purchased from Novus (Littleton, Colo.). In order to obtain full activity, cathepsin B and the tissue lysate needed to be activated in 5 mM dithiothreitol (DTT) and 25 mM 2-(4-morpholino) ethane sulfonic acid (MES) buffer (pH 5.0) right before used for proteolytic reactions. The substrate Z-Leu-Arg-AMC for fluorescence assay was obtained from Bachem (Torrance, Calif.). All aqueous solutions were prepared using 18.2 MΩ-cm resistivity deionized (DI) water from a bench-top water purifier (Barnstead EASYpure II RF/UV, Model D7035, Thermo Scientific, Asheville, N.C.). Glycine chlorotrityl resin (0.48 mmol/g; 200 mesh) was purchased from Peptides International Inc. (Louisville, Ky.).

Two types of VACNF NEAs were employed in this example, including (1) single NEA chips consisting of randomly distributed VACNFs in a forest-like configuration and (2) 3×3 multiplex NEA chips consisting of nine independently addressed regular VACNF arrays defined by e-beam lithography. The random NEA chips were readily produced and thus used for the extensive studies on method development. Limited by the high cost, e-beam patterned NEA chips were only used in experiments to demonstrate the capabilities of high-performance multiplex detection. The fabrication procedures are described below.

Figure 5:
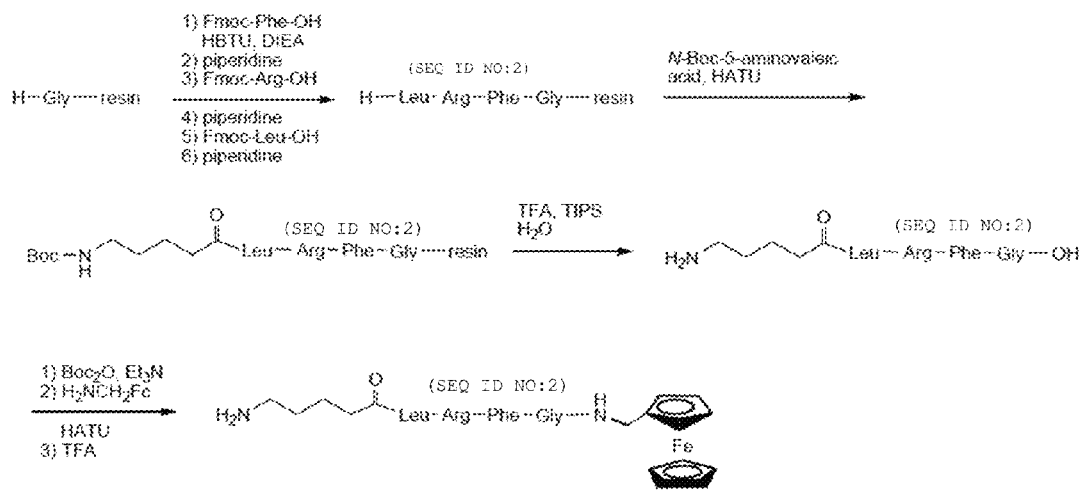
FIG. 5 illustrates the synthesis of $H_2N—(CH_2)_4CO$-(SEQ ID NO:2)-$NHCH_2$-Fc for cathepsin B detection.

Synthesis of tetrapeptide $H_2N$—$(CH_2)_4CO$-(SEQ ID NO:2)-OH was performed using a CEM microwave peptide synthesizer, and is generally shown in FIG. 5. The Glycine chlorotrityl resin (0.48 mmol/g; 200 mesh) was purchased from peptide international. The procedures for coupling, removal of Fmoc protecting group, and cleavage from the resin were identical to that described for the synthesis of legumain substrate in Example 1. From 1.2 g (0.57 mmol) of Glycine chlorotritylresin, 0.32 g (94% yield) of $H_2N$—$(CH_2)_4CO$-(SEQ ID NO:2)-OH was obtained as a white solid. MS, m/z, calcd for $C_{28}H_{47}N_8O_6$ $(M+H)^+$ 591.4, found 591.2.

Synthesis of Boc-HN—$(CH_2)_4CO$-(SEQ ID NO:2)-OH

A solution of sodium bicarbonate (86 mg, 1.2 mmol) and $H_2N$—$(CH_2)_4CO$-(SEQ ID NO:2)-OH (0.300 g, 0.5 mmol) in 30 mL of dioxane:water (1:1) was stirred at 25° C. for 10 min. To it, di-t-butyl dicarbonate (Boc$_2$O) (0.22 g, 1.2 mmol) was added, and the solution stirred for 12 h, concentrated to dryness yielding a white solid (0.35 g; 99% yield). MS calcd for $C_{33}H_{55}N_8O_8$ $(M+H)^+$ 691.4, found 691.7.

Synthesis of Boc-HN—$(CH_2)_4CO$-(SEQ ID NO:2)-NHCH$_2$-Fc

A solution of Boc-NH(CH$_2$)$_4$CO-(SEQ ID NO:2)-OH (60 mg, 0.09 mmol) and HATU (47 mg, 0.12 mmol) in DMF (2 mL) was stirred at 25° C. for 10 min. To it, aminomethylferrocene (26 mg, 0.12 mmol) was added, and the solution was stirred for 2 h, filtered, and separated on a HPLC using a preparative column (Phenomenex-Jupiter C18) and eluting with 40% acetonitrile/water to 80% acetonitrile/water over 40 min with a 10 ml/min flow rate. The fractions containing the desired product were combined and lyophilized to yield Boc-HN—$(CH_2)_4CO$-(SEQ ID NO:2)-NHCH$_2$-Fc as a yellow solid (40 mg; 50% yield). MS, m/z, calcd for $C_{44}H_{66}FeN_9O_7$ $(M+H)^+$ 888.4, found 888.6.

Synthesis of $H_2N$—$(CH_2)_4CO$-(SEQ ID NO:2)-NHCH$_2$-Fc

A solution of Boc-HN—$(CH_2)_4CO$-(SEQ ID NO:2)-NHCH$_2$-Fc (50 mg; 56 μmol) in 2 mL of 10% TFA in dichloromethane was stirred at 25° C. for 30 min, concentrated gently on a rotary evaporator, dissolved in deionized water (2 mL), frozen, and lyophilized to give H$_2$N—(CH$_2$)$_4$CO-(SEQ ID NO:2)-NHCH$_2$-Fc as a green solid (43 mg; 98% yield). MS, m/z, calcd for C$_{39}$H$_{58}$FeN$_9$O$_5$ (M+H)$^+$ 788.4, found 788.5.

Verification of the Inactivity of the Guanidine —NH Function of Arginine Residue of Boc-HN—(CH$_2$)$_4$CO-(SEQ ID NO:2)-NHCH$_2$-Fc The following reaction has been carried out to verify that the guanidine —NH function of arginine residue of Boc-HN—(CH$_2$)$_4$CO-(SEQ ID NO:2)-NHCH$_2$-Fc does not form amide bond with the carboxylic function on carbon nanofibers. To a 1 mL aqueous solution of Boc-HN—(CH$_2$)$_4$CO-(SEQ ID NO:2)-NHCH$_2$-Fc (3 mg, 3.4 µmol), benzoic acid (0.4 mg, 3.4 µmol), and N-hydroxysuccinimide (0.4 mg, 3.4 µmol) was added with 1-ethyl-3-(3-dimethylaminopropyl) carbodiimide hydrochloride (0.66 mg, 3.4 µmol), and the resulting solution was stirred at 25° C. for 2 hours. Mass spectrometry analysis showed that no reaction took place between the NH group of arginine residue and the carboxylic acid moiety of benzoic acid. Only the starting peptide was found by mass spectrometry. Boc-HN—(CH$_2$)$_4$CO-(SEQ ID NO:2)-NHCH$_2$-Fc remained unchanged. The test suggested that the NH moiety in the side chain of arginine residue does not react with the carboxylic acid function of carbon nanofibers. The most likely route for the peptide to be attached to the VACNF NEA is by forming the amide bond through the —NH$_2$ group at the distal end of the linker.

Figure 6:
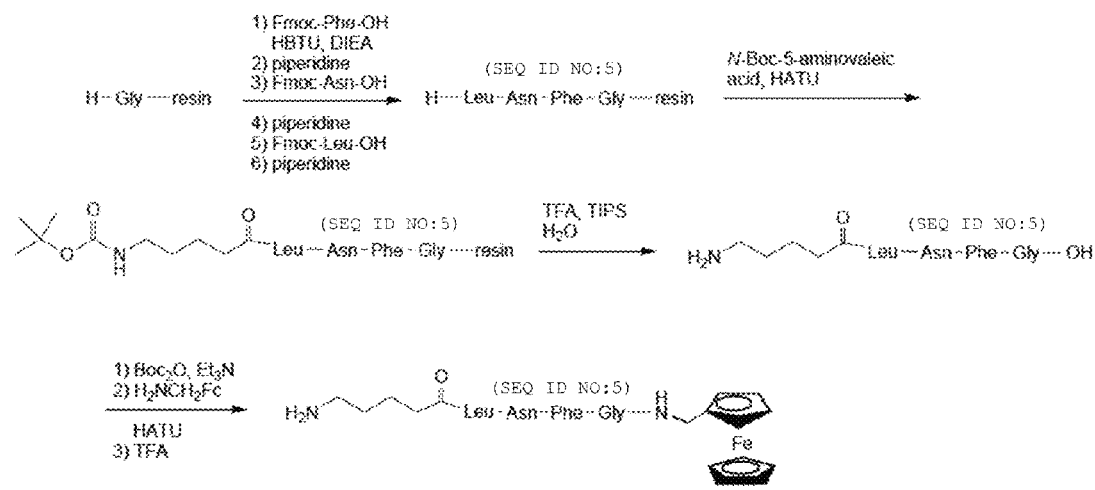
FIG. 6 illustrates the synthesis of $H_2N—(CH_2)_4CO$-(SEQ ID NO:5)-$NHCH_2$-Fc as a "negative control" tetrapeptide for the cathepsin B enzymatic study.

Synthesis of H$_2$N—(CH$_2$)$_4$CO-(SEQ ID NO:5)-NHCH$_2$-Fc as "Negative Control" Tetrapeptide for Cathepsin B Enzymatic Study Synthesis of tetrapeptide H$_2$N—(CH$_2$)$_4$CO-(SEQ ID NO:5)-OH was performed using a CEM microwave peptide synthesizer as described above and is generally shown in FIG. 6. To 1.2 g (0.57 mmol) of glycine chlorotrityl resin was added a solution of Fmoc-amino acid (1.71 mmol, 3 equiv.) and HBTU (1.55 mmol, 2.7 equiv.) in dry DMF (13 mL) containing 4.2% diisopropylethyl amine. The mixture was subjected to microwave irradiation (25 W, 5 min, 75° C.) with stirring. The reaction mixture was filtered and washed with DMF (10 mL each, 5 times). The standard procedure for the removal of Fmoc protecting group is followed. A solution of 20% piperidine in DMF (20 mL) was added to the above resin and subjected to microwave irradiation (50 W, 3 min, 75° C.). The reaction mixture was filtered and washed with DMF (10 ml each, 5 times). The standard procedure for cleavage of the peptide from resin is followed. The above resin was washed with dichloromethane (20 mL) and mixed with 20 mL of a cleavage cocktail solution consists of 95% trifluoroacetic acid (TFA), 2.5% triisopropylsilane (TIPS), and 2.5% water. The mixture was irradiated under a microwave reactor (20 W, 38° C.) for 18 min. The reaction mixture was filtered into a 100 mL flask and diluted with 100 mL of cold hexane:ether (1:1) to precipitate out the desired peptide. The solid peptide was collected by centrifugation (2500 rpm) and washed three times with cold hexane:ether (1:1) to give H$_2$N—(CH$_2$)$_4$CO-(SEQ ID NO:5)-OH as white solids (260 mg; 83% yield). $_1$H NMR (400 MHz, D$_2$O) δ 7.28-7.37 (m, 3H), 7.22-7.26 (m, 2H), 4.61-4.66 (m, 1H), 4.22-4.27 (m, 1H), 3.92 (d, J=5.47 Hz, 1H), 3.15-3.21 (m, 1H), 2.93-3.01 (m, 4H), 2.61-2.76 (m, 2H), 2.28-2.34 (m, 2H), 1.60-1.66 (m, 4H), 1.49-1.58 (m, 2H), 1.37-1.45 (m, 2H), 0.90 (d, J=6.25 Hz, 3H), 0.85 (d, J=6.64 Hz, 3H); MS, m/z, calcd for C$_{26}$H$_{41}$N$_6$O$_7$ (M+H)$_+$ 549.3, found 549.1.

Synthesis of Boc-HN—(CH$_2$)$_4$CO-(SEQ ID NO:5)-OH

A solution of sodium bicarbonate (46 mg, 0.55 mmol) and H$_2$N—(CH$_2$)$_4$CO-(SEQ ID NO:5)-OH (0.15 g, 0.27 mmol) in 20 mL of dioxane:water (1:1) was stirred at 25° C. for 10 min. To it, di-t-butyl dicarbonate (Boc$_2$O) (0.12 g, 0.55 mmol) was added, and the solution stirred for 24 h, concentrated to dryness yielding a white solid (0.18 g; 100% yield). MS, m/z, calcd for C$_{31}$H$_{48}$N$_6$O$_9$Na (M+Na)$_+$ 671.3, found 671.3.

Synthesis of Boc-HN—(CH$_2$)$_4$CO-(SEQ ID NO:5)-NHCH$_2$-Fc

A solution of Boc-NH(CH$_2$)$_4$CO-(SEQ ID NO:5)-OH (177 mg, 0.27 mmol) and HATU (115 mg, 0.30 mmol) in distilled DMF (4 mL) was stirred at 25° C. for 5 min. To it, aminomethylferrocene (65 mg, 0.30 mmol) was added, and the solution was stirred for 18 h, filtered, and separated on a HPLC using a preparative column (Phenomenex-Jupiter C18) and eluting with 40% acetonitrile/water to 80% acetonitrile/water over 40 min with a 10 ml/min flow rate. The fractions containing the desired product were combined and lyophilized to yield Boc-HN—(CH$_2$)$_4$CO-(SEQ ID NO:5)-NHCH$_2$-Fc as a yellow solid (150 mg; 65% yield). MS, m/z, calcd for C$_{42}$H$_{59}$FeN$_7$O$_8$Na (M+Na)$^+$ 868.4, found 868.4.

Synthesis of H$_2$N—(CH$_2$)$_4$CO-(SEQ ID NO:5)-NHCH$_2$-Fc

A solution of Boc-HN—(CH$_2$)$_4$CO-(SEQ ID NO:5)-NHCH$_2$-Fc (60 mg; 71 mmol) in 3 mL of 10% TFA in dichloromethane was stirred at 25° C. for 30 min, concentrated gently on a rotary evaporator, dissolved in deionized water (2 mL), frozen, and lyophilized to give H$_2$N—(CH$_2$)$_4$CO-(SEQ ID NO:5)-NHCH$_2$-Fc as a green solid (52 mg; 100% yield). $^1$H NMR (400 MHz, DMSO-d$_6$) δ 8.31 (t, J=5.66 Hz, 1H), 8.17 (d, J=7.81 Hz, 1H), 8.13 (d, J=7.81 Hz, 1H), 7.99 (d, J=7.81 Hz, 1H), 7.73 (br. s., 5H), 7.49 (br. s., 1H), 7.14-7.27 (m, 6H), 7.02 (br. s., 1H), 4.48 (q, J=6.64 Hz, 1H), 4.36-4.42 (m, 1H), 4.15-4.31 (m, 9H), 4.11 (br. s., 2H), 3.97 (br. s., 2H), 3.59-3.75 (m, 2H), 3.11 (dd, J=13.9, 4.1 Hz, 1H), 2.87 (d, J=9.76 Hz, 1H), 2.84 (d, J=9.76 Hz, 1H), 2.76 (d, J=5.86 Hz, 2H), 2.56 (d, J=6.64 Hz, 1H), 2.52 (d, J=6.64 Hz, 1H), 2.44 (d, J=6.25 Hz, 1H), 2.40 (d, J=6.64 Hz, 1H), 2.10-2.18 (m, 2H), 1.45-1.59 (m, 4H), 1.28-1.44 (m, 2H), 0.86 (d, J=6.64 Hz, 3H), 0.82 (d, J=6.25 Hz, 3H); $^{13}$C NMR (100 MHz, DMSO-d$_6$) δ 172.9, 172.7, 172.6, 171.8, 171.7, 168.7, 138.6, 129.7, 128.7, 126.9, 86.6, 69.1, 68.4, 68.0, 55.1, 51.5, 50.3, 42.9, 41.4, 39.3, 38.2, 37.4, 35.0, 27.3, 24.9, 23.8, 22.7, 22.1; MS, m/z, calcd for C$_{37}$H$_{52}$FeN$_7$O$_6$ (M+H)$^+$ 746.3, found 746.2.

Fabrication of VACNF NEA Chips

The NEAs were fabricated by encapsulating VACNFs in SiO$_2$ matrix on a silicon chip using a similar method described in Example 1. Briefly, VACNFs of an average length of 5 µm were grown on ~100 nm Cr coated Si substrate using a DC-biased plasma enhanced chemical vapor deposition (PECVD) system (Aixtron, Calif.). A thin nickel film of ~22 nm was used as the catalyst to promote CNF growth. The electric field helped to align the CNF vertically on the substrate surface. Cross-sectional SEM images indicate that about 90% of the CNF have the length of 4 to 6 microns. The CNFs have the diameter distributed from ~100 to 200 nm and are well separated from each other, with an average distance of ~300 to 400 nm. Dielectric $SiO_2$ was deposited using chemical vapor deposition (CVD) from vapor-phase precursor tetraethylorthosilicate (TEOS) to fully encapsulate the bottom Cr metal contact layer and each individual CNFs. Mechanical polishing was applied using 0.3 μm alumina slurry to produce a flat surface. Reactive ion etching (RIE) with a mixture of $CHF_3$ and $O_2$ gases was then performed with NRE-3000 (Nano-Master Inc., Austin, Tex.) to selectively etch away desired amount of $SiO_2$. It can be controlled to expose 20% to 60% of the CNF tips based on the length variation. A typical random patterned VACNF NEA in this study consists of randomly distributed CNF tips with an average CNF diameter of ~100-200 nm and an average spacing over ~1 μm (corresponding to a density of ~(1-10)×10$^7$ CNFs·cm$^{-2}$). The length of exposed CNF tips was controlled at ~50-300 nm by varying the RIE time to selectively remove $SiO_2$.

Figure 7:
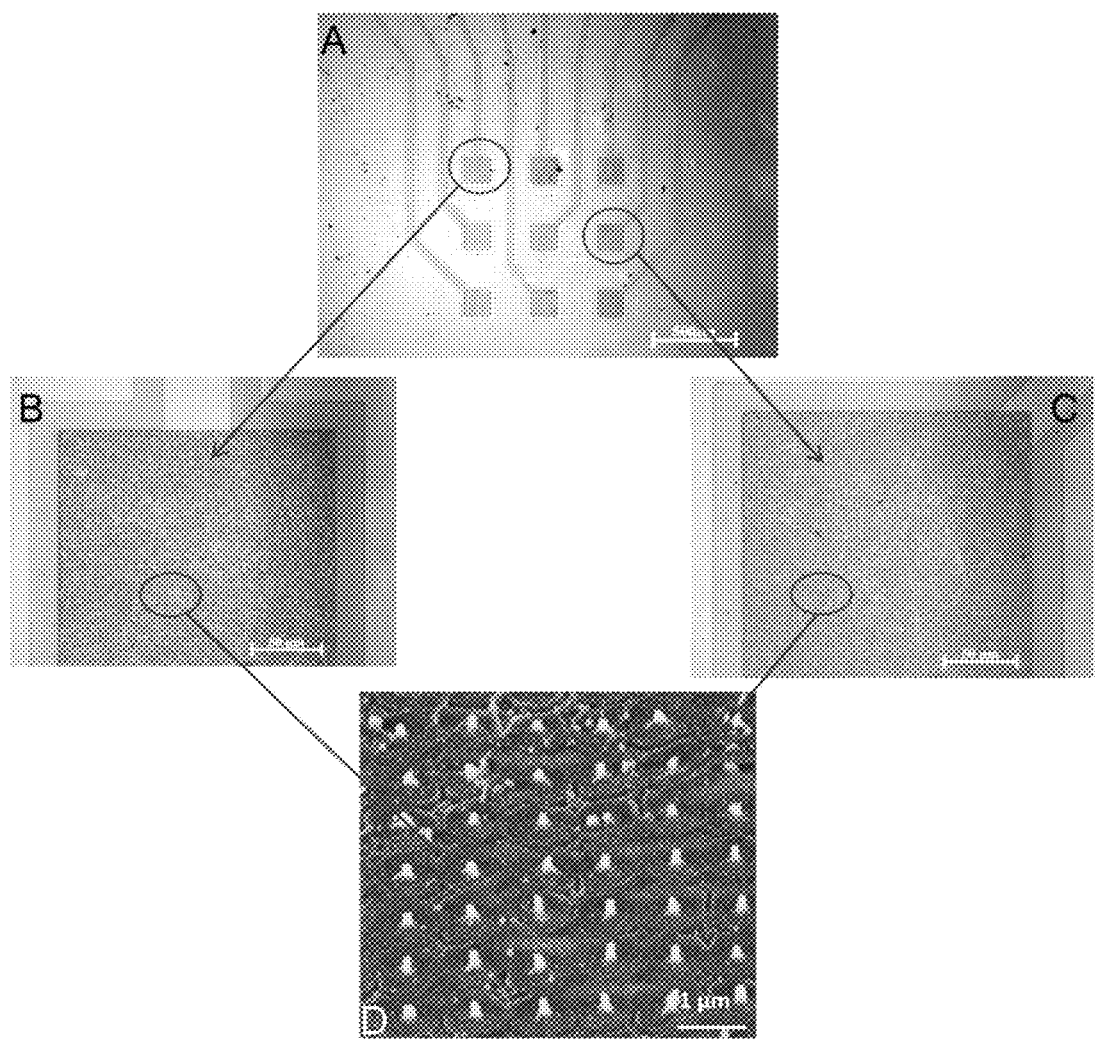
FIG. 7 shows bright field microscope images of patterned VACNF NEAs with (A) using a 4× objective lens, (B) and (C) using a 50× objective lens, and (D) Field-emission scanning electron microscopy image at 45° perspective view of the patterned VACNF NEAs (scale bars=500, 50, 50, and 1 μm, respectively)

As shown in FIG. 7, the multiplex chip comprised 3×3 independently addressed microelectrodes (with the active areas of 200 μm×200 μm) as well as the connecting lines and the nine contact pads on top (1 mm×1 mm in lateral size), which were patterned 100 nm thick Cr films on a 500 nm thick $SiO_2$ covered 4" Si wafer. The pattern was defined by an UV-lithography and a lift-off metallization process. The 200 μm×200 μm microelectrode areas were further deposited with Ni catalyst dots (~100 nm in diameter, 30 nm in thickness) with a regular 1.0 μm square lattice defined by e-beam lithography patterning in a 200 nm thick poly (methyl methacrylate) (PMMA) photoresist layer followed with a liftoff process. VACNFs of ~3 micron in length were then grown on these chips by PECVD with mixed precursors ($C_2H_2$ and $NH_3$) was then used to grow VACNFs on these chips following the similar procedure reported before. Generally, over 90% of the sites showed one CNF grown from a single Ni dot. The CNF diameter was uniformly defined as ~100 nm, matching the size of the e-beam patterned Ni dots. A plasmon-enhanced TOES CVD was used to deposit ~2 micron thick $SiO_2$ to encapsulate the VACNFs and the chip surface. A brief chemical mechanical polishing was then applied to planarize the surface by breaking VACNFs at the surface of $SiO_2$ matrix. To selectively expose the 1 mm×1 mm contact pads, the chip was patterned with an UV lithography using a 2.5 μm thick Shipley 3012 resist and wet etching with a 7:1 diluted HF solution was applied to remove only the $SiO_2$ at the contact pads. The rest of the photoresist was then removed using EKC 830 resist stripper in 15 min. Before each experiment, the chip was then subjected to proper RIE with a mixture of CHF3 and $O_2$ to remove the $SiO_2$ matrix around the VACNFs and exposed desired length of the VACNFs. In this study, the exposed length of each CNF was uniformly controlled around 150 nm. Overall, the e-beam patterned regular VACNF NEAs in the 3×3 multiplex chips had much more uniform structure and more consistent electrochemical properties than the random VACNF NEAs, which are desired for future applications.

Electrode Pre-Conditioning

The VACNF NEA chip needed to be preconditioned before each use. The random VACNF NEAs were polished with 0.05-μm γ-alumina slurry on napless polishing cloth (Buehler, Lake Bluff, Ill.) for 5-15 min, followed by rinsing with deionized water. The e-beam patterned regular VACNF NEA chip was treated with 30 s of $O_2$ reactive ion etching (RIE) (NANO-MASTER Inc, Austin, Tex.) to clean the chip surface and then followed by 4 min of RIE with a mixture flow of $CHF_3$ and $O_2$ (at 10.0 and 2.0 sccm, respectively) to remove ~200 nm thickness of $SiO_2$. Both types of VACNF NEAs were then electrochemically activated by etching in 1.0M NaOH solution using four cycles of CV in a potential range of −0.10 V to 1.20 V (vs. Ag/AgCl (3M KCl)) at a scan rate of 50 mV·s$^{-1}$.

Passivation of the $SiO_2$ Surface of the VACNF NEA Chip

To reduce nonspecific adsorption, the $SiO_2$ surface of the VACNF NEAs was first passivated with protective moieties containing ethylene glycol. The chip was immersed in an 8 g·L$^{-1}$ solution of APTES in ethanol for 20 min to produce a primary amine derivatized surface. The chip was treated with 50 μL solution of 0.1 mM of 2-(2-methoxyethoxy) ethoxyacetic acid, 100 g·L$^{-1}$ of EDC and 50 g·L$^{-1}$ of sulfo-NHS, and incubated at 25° C. for 2 h in a closed chamber (Arrayit, Calif.). The carboxylic acid group of 2-(2-methoxyethoxy)ethoxyacetic acid formed an amide bond with the amino function on the chip surface, leaving ethylene glycol moiety at the top surface. The molecules attached to the CNF tips were then removed by electrochemical etching at 1.2 V (vs. Ag/AgCl (3M KCl)) for 20 s in 1.0M NaOH solution. This process regenerated clean CNF tips which contained abundant carboxylic acid functional groups.

Functionalization of Fc-Peptide to the VACNF NEA Chip

The Fc-appended tetrapeptides was covalently linked to the VACNF NEA through a $(CH_2)_4NH_2$ linker by forming amide bond facilitated by 1-ethyl-3-(3-dimethylaminopropyl)carbodiimide hydrochloride (EDC) and sodium 1-hydroxy-2,5-dioxopyrrolidine-3-sulfonate (sulfo-NHS). Typically, a 10 μL solution consisting of 10 mM tetrapeptide mixed with 90 μL of 10 g·L$^{-1}$ EDC and 10 g·L$^{-1}$ sulfo-NHS was applied onto the electrochemically activated VACNF NEA chip and incubated in a closed Arrayit chamber at 25° C. for 2 h. Control experiments and HPLC-MS characterization in our previous report confirmed that only the end —NH$_2$ group of the tetrapeptide formed amide bond with the carboxylic acid group on the VACNF NEA. (Swisher et al. 2013) The —NH$_2$ and NH functions of the guanidine group in arginine residue in the tetrapeptide did not react with the carboxylic acid group under the reaction conditions. In order to stabilize the electronic signal, the CNF electrode surface was further dipped into 5.0 mL solution containing a diluent agent (1.0 mM 6-amino-1-hexanol) and the coupling agents (5.0 g·L$^{-1}$ EDC, and 2.0 g·L$^{-1}$ sulfo-NHS) so that the unreacted —COOH sites were linked with 6-aminohexanol.

Western Blot Analysis and Immunoprecipitation Assay

Expression of cathepsin B in human breast tissue lysate (25 μg) was analyzed by Western blot using cathepsin B antibody. Furthermore, 0.5 mg of the tissue lysate was used for immunoprecipitation assay using cathepsin B antibody. The immunoprecipitated fraction (in pellet) and the supernatant fraction after four rounds of immunoprecipitation were subjected to Western blot analysis using cathepsin B antibody. The results show that cathepsin B was largely removed from tissue lysate. The proenzyme cathepsin B was ~37 kDa and the active cathepsin B was ~25 kDa.

The electrochemical measurements with random VACNF NEAs were performed in a TEFLON cell with a total volume of 250 μL that was sealed against the VACNF NEA chip with a 3-mm i.d. O-ring. The measurements with e-beam patterned multiplex chips were carried out with a larger polycarbonate cell sealed against the chip with an 8-mm i.d. O-ring. All nine microelectrode pads were exposed to the solution. All measurements used three electrode configuration with a VACNF NEA working electrode, an Ag/AgCl (3M KCl) reference electrode, and a coiled Pt wire counter electrode. The electrolyte solution for proteolytic measurements was 25 mM MES (pH=5.0). The ACV was measured by applying a 800 Hz and 150 mV amplitude AC voltage on the DC staircase waveform sweeping from −0.1 V to +0.75 V at 10 mV s$^{-1}$ scan rate.

The activities of the enzymes vary significantly from batch to batch and are very sensitive to the environment and storage conditions. To reduce errors, the enzyme activities were first validated with a commercial fluorescence-based biochemical method using a substrate benzyloxycarbonyl-Leucine-Arginine-7-amino-4-methylcoumarin (Z-Leu-Arg-AMC) (Bachem, Torrance, Calif.) before each electrochemical experiment. The cleavage to the substrate at the site between arginine and AMC dye released AMC from quenching by the carbonyl group and thus gave increased fluorescence intensity.

Results

The tetrapeptides (SEQ ID NO:2) labeled with electroactive Fc at the distal end are immobilized on the VACNF NEAs. Fc provides a reliable oxidation peak at ~0.25 V versus Ag/AgCl (3M KCl) in ACV measurements. Cathepsin B specifically cleaved the tetrapeptide at the site between arginine and phenylalanine. This releases the fragment containing Fc into the bulk solution and caused the peak current to decrease. The kinetics of the proteolytic reaction is monitored with continuously repeated ACV measurements. A noteworthy advantage of ACV technique on Fc-attached VACNF NEAs is that the optimum AC frequency (800-1800 Hz) was much higher than that on macro-GCEs (~40 Hz), leading to higher sensitivity and higher temporal resolution.

For $H_2N-(CH_2)_4-CO$-(SEQ ID NO:2)-$NH-CH_2$-Fc immobilized on a random VACNF NEA a representative ACV curve was generated. The AC peak current $i_{p,acv}$ can be derived by subtracting a linear background. Four representative background-subtracted ACV curves corresponding to 0, 20, 40 and 60 min, respectively, were prepared after adding the purified cathepsin B solution at three different final concentrations. The background-subtracted peak current $i_{p,acv}$ clearly decreased with the reaction time while the peak position slowly shifted from ~0.25 to ~0.15 V. The value of $i_{p,acv}$ from all ACVs versus the reaction time t were plotted. The value of $i_{p,acv}$ was relatively stable at the beginning. Adding the cathepsin B solution at t=0 caused some disturbance to the $i_{p,acv}$ signal. Following that, all curves showed an exponential decay versus the reaction time, which can be fitted with $$i_t = i_0 \exp(-t/\tau) + (bt+c). \qquad (1)$$

The values of the fitting parameters to the plots of $i_{p,acv}$ versus time for all ACVs are listed in Table 1, below.

TABLE 1

| [Cathepsin B] | Fitting Equation: $i_t = i_0 \exp(-t/\tau) + (bt + c)$ | | | |
|---|---|---|---|---|
| (nM) | i0 (A) | b (A/s) | c (A) | (s) |
| 15.5 | 6.69 × 10$^{-7}$ | −4.12 × 10$^{-11}$ | 8.11 × 10$^{-7}$ | 2935 |
| 30.7 | 8.35 × 10$^{-7}$ | −3.33 × 10$^{-11}$ | 1.03 × 10$^{-7}$ | 1287 |
| 62.1 | 7.22 × 10$^{-7}$ | −4.55 × 10$^{-11}$ | 4.35 × 10$^{-7}$ | 448 |

The value of $i_0$ correlated with the total amount of surface-functionalized peptide-Fc, which varied with the density and exposed length of VACNFs in the NEAs. The term (bt+c) was found due to the Fc residues that were not cleavable by the protease. A large portion of them was attributed to physically trapped peptide-Fc at the Cr or embedded CNF surface due to the defects and pores in the $SiO_2$ insulating layer. There was also a possibility that some covalently attached peptide-Fc molecules might lie tightly on the VACNF surface and cannot be cleaved by the protease due to the steric hindrance. Both factors may lead to the negative shift of ACV peak potential.

Two "negative control" experiments were carried out to ascertain that the exponential decay of the $i_{p,acv}$ signal was attributed to the specific proteolysis of cathepsin B by using a non-relevant peptide-Fc substrate $H_2N-(CH_2)_4-CO$-(SEQ ID NO:1)-$NH-CH_2$-Fc and a peptide-Fc substrate with the specific cleavage site (i.e, P1) -Arg- replaced by -Asn-, i.e., $H_2N-(CH_2)_4-CO$-(SEQ ID NO:5)-$NH-CH_2$-Fc. The peak current $i_{p,acv}$ of these two tetrapeptides did not show the characteristic exponential decay while the activated cathepsin B was added into the electrochemical cell. Apparently, the exponential decay of the $i_{p,acv}$ value after adding the protease represents the proteolysis kinetics. However, the raw $i_{p,acv}(t)$ values cannot be directly compared due to the variations in Fc-peptide quantity and background level from sample to sample. In order to normalize these varying factors, we define a new function S, referred as "extracted proteolytic signal", with $$S = [i_t - (bt+c)]/i_0 = \exp(-t/\tau). \qquad (2)$$

The extracted function S is essentially the exponential component of the kinetic data, whose decay time constant $\tau$ is directly related to the protease activity, as will be discussed later. The proteolytic measurements of different random VACNF NEAs at three cathepsin B concentrations were normalized to the same fractional scale using S, with all curves passing through (t=0, S=1.0). This allowed clear view of the decay rate from different samples. The increase in cathepsin B concentration caused the function S to decay faster, giving smaller decay time constant $\tau$ and higher protease activity. This new method is critical for later studies requiring quantitative comparison of data from a large set of electrodes.

The proteolysis kinetics can be analyzed with a modified Michaelis-Menten model for heterogeneous enzymatic reactions $$E + S_s \underset{k_{-1}}{\overset{k_1}{\rightleftharpoons}} ES_s \overset{k_{cat}}{\longrightarrow} E + P_s + P, \qquad (3)$$

where E, $S_s$, $ES_s$, $P_s$ and P represent the enzyme, surface-bound peptide substrate, enzyme-substrate complex on the electrode surface, surface-attached product, and product released to solution, respectively. The reaction rate υ can be defined as

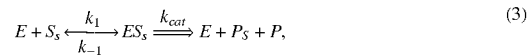

where $\Gamma_{Ss}$ represents the surface density of active peptide substrate, $k_{cat}$ is the dissociation rate constant and $K_M = (k_{cat}+k_{-1})/k_1$ is the Michaelis-Menten constant, respectively. Since "extracted proteolytic signal" S is proportional to the surface densities of Fc-peptide substrates (i.e., $\Gamma_{Ss} \propto S$), Eq. (4) can be rewritten as Eq. (5) and, at low enzyme concentrations ($[E_0] \ll KM$), an approximate relationship can be obtained as $$\upsilon \propto -\frac{dS}{dt} = \frac{K_{cat}[E_0] \times S}{K_M + [E_0]} \approx \frac{K_{cat}[E_0] \times S}{K_M}, \quad (5)$$

The value of (~dS/dt) can be derived from FIG. 2 and plot versus S in FIG. 3A. Combining Eqs. (2) and (5), it gives $$-\frac{dS/dt}{S} = \frac{k_{cat}}{K_M}[E_0] = \frac{1}{\tau}. \quad (6)$$

Therefore, the measured quantity $(k_{cat}/K_M) \cdot [E_0]$ can be represented by $1/\tau$ or the slope of the plots of the reaction rate $-dS/dt$ versus extracted proteolysis signal $S=(i_t-i_b)/i_0$ at different cathepsin B concentrations, with smaller t giving larger $(kcat/KM) \sim [E_0]$. The statistical value of $(k_{cat}/K_M) \cdot [E_0]$ derived from the slope of each of these plots (i.e., $-dS/dt$ versus S) was $(7.45\pm3.53) \times 10^{-4}$, $(1.25\pm0.30) \times 10^{-3}$ and $(2.15\pm0.37) \times 10^{-3}$ s$^{-1}$ from nine experiments with enzyme concentration at 15.5, 30.7 and 62.1 nM, respectively. The derived quantity $(k_{cat}/K_M) \cdot [E_0]$ is linearly proportional to the enzyme concentration $[E_0]$, consistent with the theoretical model. Since $[E_0]$ was known in previous measurements, one can easily derive the concentration-independent "specificity constant" $k_{cat}/K_M$ which is commonly used to represent the fundamental catalytic efficiency of different enzymes.

The calculated $k_{cat}/K_M$ values at three cathepsin B concentrations were very close to each other, giving an average value of $4.11 \times 10^4$ M$^{-1}$ s$^{-1}$ and a standard deviation of $6.66 \times 10^3$ M$^{-1}$ s$^{-1}$. Alternatively, fitting the data points in the plot of $(k_{cat}/K_M) \cdot [E_0]$ with a straight line passing through the origin gave a more accurate $k_{cat}/K_M$ value of $(3.68\pm0.50) \times 10^4$ M$^{-1}$ s$^{-1}$ that incorporated the results from all nine experiments at three discrete cathepsin B concentrations. These $k_{cat}/K_M$ values are more accurate than previous analyses based on ACV measurements at a single enzyme concentration. The $k_{cat}/K_M$ of the same batch of cathepsin B derived from nine fluorescence experiments right before the electrochemical measurements was $(9.6\pm4.1) \times 10^4$ M$^{-1}$ s$^{-1}$, showing much larger standard deviation. Importantly, the results confirmed that the $k_{cat}/K_M$ value by ACV measurements remained constant as the cathepsin B concentration varied, establishing a method to determine the cathepsin B activity in an unknown sample by dividing the measured $(k_{cat}/K_M) \cdot [E_0]$ with the above $k_{cat}/K_M$ value.

Normal human tissues may contain many proteases including cathepsin B and their expression at higher level is expected in cancerous tissues. To demonstrate that ACV coupled with VACNF NEAs is viable for detecting protease activities in complex human samples, three sets of measurements using lysates from human breast tissue have been carried out. The cathepsin-B-specific tetrapeptide H$_2$N—(CH$_2$)$_4$CO-(SEQ ID NO:2)-NH—CH$_2$-Fc was immobilized on random VACNF NEAs. The human breast whole tissue lysate (adult normal) was first treated with the activation buffer similar to the purified cathepsin B experiments. 25 mL of the activated lysate solution was then added into the electrochemical cell containing 250 µL of 25 mM MES (pH 5.0) while the ACV measurement was continuously repeated. The final concentrations of the lysate were 20.0 µg·mL$^{-1}$ and 29.1 µg·mL$^{-1}$, diluted by 245 and 168 fold, respectively from the purchased tissue lysate stock solution. Both lysate samples caused exponential decay after being added into the electrochemical cell, as shown in the "extracted proteolytic signal" $S=(i_t-i_b)/i_0$ with $i_b=bt+c$. The fitted time constants are $\tau_0=725$ s and $\tau_0=1647$ s at the lysate concentration of 29.1 and 20.0 µg·mL$^{-1}$, respectively. The derived $(k_{cat}/K_M) \cdot [E_0]$ values are $6.04 \times 10^{-4}$ s$^{-1}$ for 20.0 µg·mL$^{-1}$ tissue lysate and much higher at $1.38 \times 10^{-3}$ s$^{-1}$ for 29.1 µg·mL$^{-1}$ tissue lysate. Using $k_{cat}/K_M=(3.68\pm0.50) \times 10^4$ M$^{-1}$ s$^{-1}$ derived from the purified cathepsin B solutions above, the equivalent cathepsin B concentrations were calculated as $\sim(16.4\pm2.2)$ nM in the 20.0 µg·mL$^{-1}$ tissue lysate, and $\sim(37.5\pm5.1)$ nM in the 29.1 µg·mL$^{-1}$ tissue lysate. Due to the existence of the experimental deviation and activity variation of biology sample, they did not present a perfect linear relationship but were close.

As 15.5 and 30.7 nM purified cathepsin B were spiked into the 29.1 mg mL$^{-1}$ tissue lysate, the decay became faster, giving $\tau_1=433$ s and $\tau_2=213$ s, respectively. Clearly, substantial proteolysis was catalyzed by cathepsin B. To further confirm that the measured decay was from the specific proteolysis of peptide-Fc by cathepsin B, an immunoprecipitation (IP) assay was employed to partially remove cathepsin B from the tissue lysate. The exponential decay was indeed much slower, giving $\tau_4=1246$ s, but some substantial decay feature was retained. It is likely that some cathepsin B still retained in the tissue lysate after four rounds of IP but the level was below the sensitivity of Western blot analysis. It is also possible that other proteases (particular other cathepsins, such as cathepsin L and V) may cleave the tetrapeptide although the catalytic activity may be lower. Quantitative estimation of cathepsin B activity in the tissue lysate can be made based on the results of the proteolysis curve. First, according to Eq. (6), the difference between the 15.5 nM spiked and unspiked samples can be derived as follows:

$$(k_{cat}/K_M)(E_0)+15.5 \text{ nM})-k_{cat}/K_M)(E_0)=1/\tau_1-1/\tau_0=9.30 \times 10^{-4} \text{ s}^{-1}, \quad (7)$$

which gives $k_{cat}/K_M=6.0 \times 10^4$ M$^{-1}$ s$^{-1}$. This value is slightly higher than the value $(4.11\pm0.67) \times 10^4$ M$^{-1}$ s$^{-1}$ obtained with purified cathepsin B in buffer solutions as discussed above. For the tissue lysates with and without IP procedure, there is $$(k_{cat}/K_M)\Delta(E_0)=1/\tau_0-1/\tau_4=5.77 \times 10^{-4} \text{ s}^{-1} \quad (8)$$

Thus the difference in cathepsin B concentration $\Delta[E_0]$ is equivalent to $\sim14\pm2.3$ nM cathepsin B in buffer solution if the value $k_{cat}/K_M=(4.11\pm0.67) \times 10^4$ M$^{-1}$ s$^{-1}$, discussed above, is used. Though refinements are needed to reduce the error bar, it is clear that this method is applicable in complex tissue lysate samples. This study established a critical step toward developing meaningful diagnosis tools. This is believed to be the first time that the activity of a protease has been quantitatively determined by electrochemical methods with complex whole tissue lysates.

The cathepsin B activity in the normal human breast whole tissue lysate was also validated by the fluorescence method using a short peptide substrate Z-Leu-Arg-AMC. This analysis yielded a very small exponential curvature giving a much lower value of $(k_{cat}/K_M) \cdot [E_0](\sim4.98 \times 10^{-5}$ s$^{-1})$ than that obtained from the electrochemical measurement $(\sim1.38 \times 10^{-3}$ s$^{-1})$, although the lysate concentration was much higher (0.24 mg mL$^{-1}$ versus 29.1 µg·mL$^{-1}$). But the lysates spiked with 11.9 and 23.9 nM purified cathepsin B showed clear exponential increases in fluorescence signal due to proteolysis, which validated that the electrochemical signal was indeed due to cathepsin B.

In the long term, regular VACNF NEAs can be mass-produced as multiplex chips on independently addressed microelectrode pads using UV- and e-beam lithography.

Figure 8:
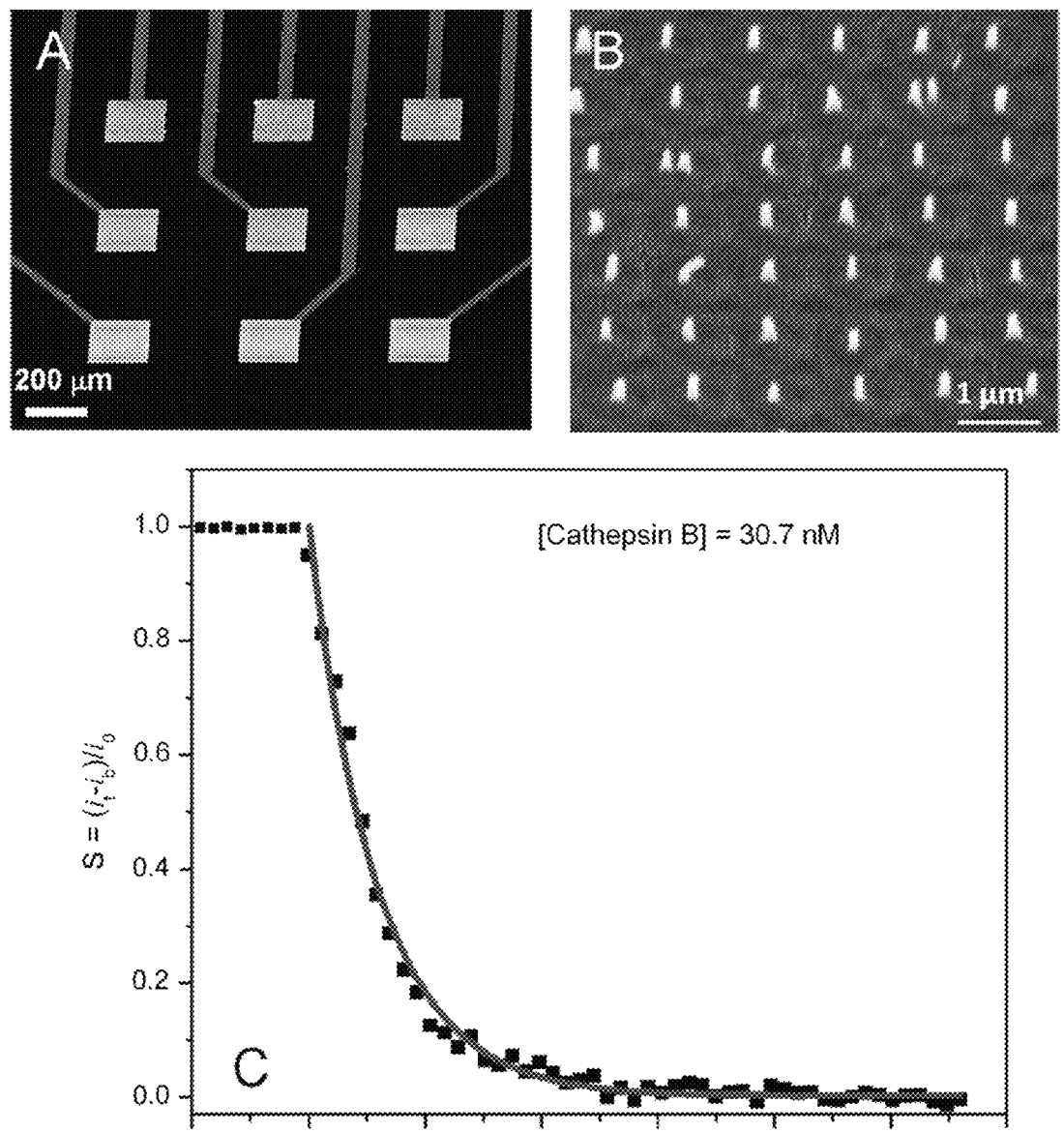
FIG. 8 illustrates SEM images at 45° perspective view of (A) a 3×3 VACNF NEA chip and (B) the e-beam patterned regular VACNF NEA partially embedded in $SiO_2$ matrix at each microelectrode pad, and (C) the extracted proteolysis signal $S=(i_r-i_b)/i_0$ was derived from continuously repeated ACV measurements while 25 μL of purified cathepsin B was added into the electrochemical cell to a final concentration of 30.7 nM (0.9 ng $μL^{-1}$), all ACV measurements were carried out at f 800 Hz and AC voltage amplitude $V_0=150$ mV.

Such chips can be integrated into portable electronic systems for profiling a set of proteases. FIG. 8A shows nine 200×200 µm² microelectrode pads of ~100 nm-thick Cr film in a 3×3 array on a SiO$_2$-covered Si wafer. VACNFs were grown in regular 1×1 µm² lattice on these microelectrode pads to form embedded NEAs which were independently connected with the measuring circuits through larger (1×1 mm²) contact pads (not shown). FIG. 8B shows the zoom-in image of exposed VACNF tips of ~100 nm in diameter and ~150 nm length protruding over the SiO$_2$ matrix. Plots of the CVs of a 50 mM K$_3$Fe(CN)$_6$ solution from all nine VACNF NEAs indicated that they all showed the characteristic sigmoidal shape with low background and almost identical limiting current, indicating the high uniformity of these NEAs.

The covalently attached tetrapeptide H$_2$N—(CH$_2$)$_4$CO-(SEQ ID NO:2)-NH—CH$_2$-Fc on the e-beam patterned regular VACNF NEA present a similar ACV peak at ~0.25 V. The peak shape was much better defined than the random VACNF NEAs. Similar as before, the ACV peak can be extracted by subtracting a linear background. The ACV peak current monotonically decreased after a purified cathepsin B solution was added into the electrochemical cell to give a final concentration of 30.7 nM. The peak potential also continuously downshifted to ~0.10 V. The completed kinetic curve of raw $i_{p,acv}$ during proteolysis showed that the $i_{p,acv}$ amplitude decayed much faster in the initial reaction period but then leveled off after ~35 min. Similar to the random VACNF NEAs, the leveled $i_{p,acv}$ was attributed to physically trapped peptide-Fc in the SiO$_2$ matrix as confirmed by the control experiment. While such background can be reduced by improving SiO$_2$ deposition and passivation, it can be easily excluded using the "extracted proteolysis signal" $S=(i_t-i_b)/i_0$ discussed earlier.

The kinetic curves of S versus the reaction time after adding 30.7 nM purified cathepsin B is shown in FIG. 8C. The fitted exponential decay time constant τ was 353 s, clearly smaller than 800±192 s obtained with random VACNF NEAs at the same cathepsin B concentration. From either the fitted slope of −dS/dt versus S or τ value, ($k_{cat}/K_M$)·[E$_0$] was calculated as 2.81×10$^{-3}$ s$^{-1}$, about twice of the statistical value (1.25±0.30)×10$^{-3}$ s$^{-1}$ on the random VACNF NEA at 30.7 nM cathepsin B concentration. Accordingly, the specificity constant $k_{cat}/K_M$ was 9.2×10$^4$, about twice of (4.11±0.67)×10$^4$ M$^{-1}$ s$^{-1}$ measured with random VACNF NEAs. Clearly, the regular VACNF NEAs worked much better than the random VACNF NEAs. The smaller diameter (~100 nm versus 150 nm) may help to reduce the steric hindrance for enzymes to interact with the immobilized peptide. The uniform size and exposed length as well as the regular spacing of the CNFs made the regular VACNF NEAs more reproducible and perform better than the random VACNF NEAs.

Example 3

In this example, ACV techniques on VACNF NEAs were applied to demonstrate the possible values of cathepsin B concentrations and activities in breast cancer cell lysates and their correlation with stages of the breast cancer for the first time. The results showed that this electrochemical method has great potential as a portable multiplex system for simple and rapid protease profiling of lysate, serum or urine samples for cancer early diagnosis and treatment monitoring.

Materials

The electrochemical measurements were carried out with an electrochemical analyzer (Model 440A, CH Instruments, Austin, Tex.). Fluorescence assay was performed on Glo-Max-Multi+Microplate Multimode Reader (Promega, Madison, Wis.) with black polystyrene 96 well plates obtained from Whatman (Picataway, N.J.). 3-Aminopropyl-triethoxysilane (APTES), 2-(2-methoxyethoxy)ethoxyacetic acid, 1-ethyl-3-(3-dimethylaminopropyl)carbodiimide hydrochloride (EDC), 1-hydroxy-2,5-dioxopyrrolidine-3-sulfonic acid sodium salt (sulfo-NHS), sodium hydroxide, and 6-amino-1-hexanol were purchased from Sigma-Aldrich (Saint Louis, Mo.). 2-(4-Morpholino)ethane sulfonic acid (MES) and dithiothreitol (DTT) were purchased from Thermo Fisher Scientific (Fair Lawn, N.J.). Purified recombinant human cathepsin B [molecular weight of 37 kDa (pro) & 29 kDa (mature)] was purchased from R&D Systems Inc. (Minneapolis, Minn.). Human breast whole tissue lysate (adult normal) with the stock concentration of 4.9 mg·mL$^{-1}$ was purchased from Novus (Littleton, Colo.). Breast cells include human mammary epithelial cells (HMEC) from Lonza (Allendale, N.J.), transformed breast cells (MCF-10A), breast cancer cells (T47D and MDA-MB-231) from American Type Cell Culture (ATCC) (Manassas, Mass., USA). Cathepsin B and the breast cells were activated in 5 mM dithiothreitol (DTT) and 25 mM 2-(4-morpholino)ethane sulfonic acid (MES) buffer (pH 5.0) right before used for proteolytic reactions. The substrate Z-Leu-Arg-AMC for fluorescence assay was obtained from Bachem (Torrance, Calif.). All aqueous solutions were prepared using 18.2 MΩ-cm resistivity deionized (DI) water from a bench-top water purifier (Barnstead EASYpure II RF/UV, Model D7035, Thermo Scientific, Asheville, N.C.). Glycine chlorotrityl resin (0.48 mmol/g; 200 mesh) was purchased from Peptides International Inc. (Louisville, Ky.). 1-[Bis(dimethylamino)methylene]-1H-1,2,3-triazolo[4,5-b] pyridinium 3-oxid hexafluorophosphate (HATU), 3-(3-dimethylaminopropyl)-1-ethylcarbodiimide (EDC), and Boc-amino acids were purchased from Chem-Impex International. The details of the synthesis of cathepsin B specific tetrapeptide H$_2$N—(CH$_2$)$_4$—CO-(SEQ ID NO:2)-NH—CH$_2$-Fc and other peptides including tripeptide Arg-Phe-Gly-NH—CH$_2$-Fc, dipeptide Phe-Gly-NH—CH$_2$-Fc and monopeptide Gly-NH—CH$_2$-Fc for studying cleaving sites by the proteases in cancer cells are described below.

Figure 9:
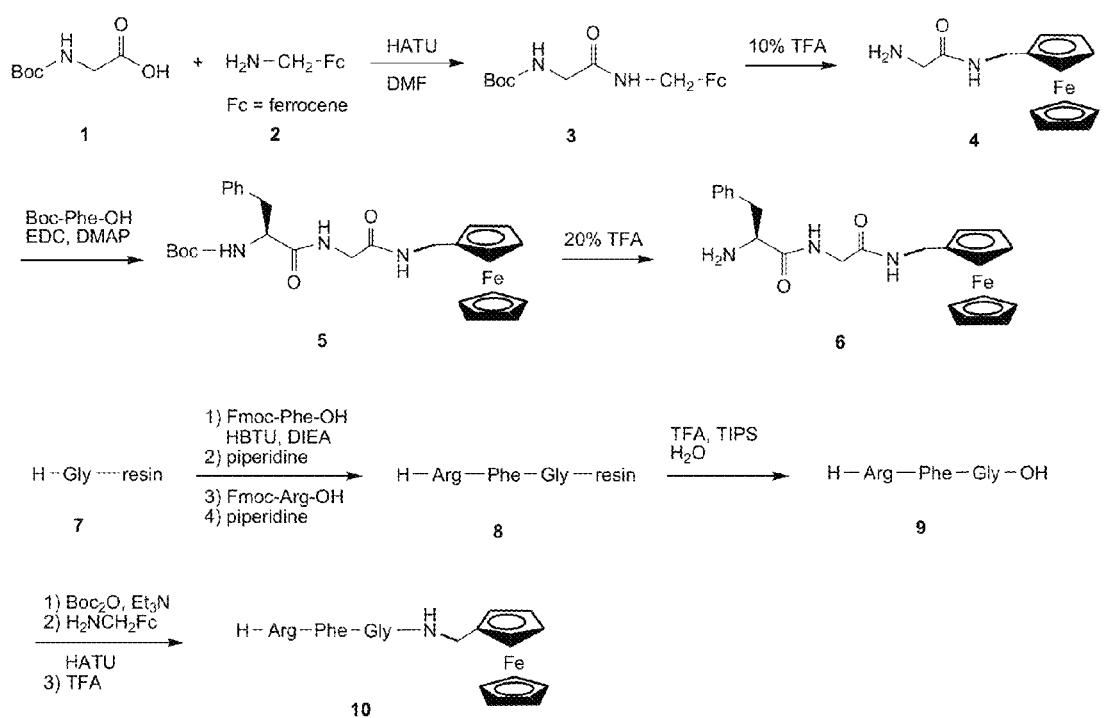
FIG. 9 illustrates the syntheses of ferrocene attached monopeptide (4), dipeptide (6), and tripeptide (10)

The synthesis of Gly-NH—CH$_2$-Fc (4), bipeptide Phe-Gly-NH—CH$_2$-Fc (6) and tripeptide Arg-Phe-Gly-NH—CH$_2$-Fc (10) are depicted in FIG. 9.

2-Amino-N-(ferrocenylmethyl)acetamide (4)

To a solution of 0.10 g (0.57 mmol) of Boc-Gly-OH (1) in 3 mL of DMF (distilled from CaH$_2$) under argon, were added 0.22 g (0.57 mmol) of HATU and 0.12 g (0.57 mmol) of (aminomethyl)ferrocene sequentially. The solution was stirred at 25° C. for 12 h, diluted with 100 mL of water, and extracted twice with dichloromethane (100 mL each). The combined extracts were washed with brine, dried (MgSO$_4$), concentrated, and column chromatographed on silica gel using a gradient mixture of dichloromethane and methanol to give 85 mg (40% yield) of compound 3. $^1$H NMR (CDCl$_3$) δ 6.32 (br s, 1H, NH), 5.10 (br s, 1H, NH), 4.17 (s, 5H, Fc), 4.15 (m, 4H, Fc), 4.14 (s, 2H, CH$_2$), 3.80 (d, J=6 Hz, 2H, CH$_2$), 1.45 (s, 9H, t-Bu); MS, electrospray ionization, m/z calcd for C$_{18}$H$_{24}$FeN$_2$NaO$_3$ (M+Na)$^+$ 395.1, found 395.1.

A solution of 85 mg of compound 3 in 10% trifluoroacetic acid (TFA) in dichloromethane was stirred at 25° C. for 30 minutes and concentrated to dryness to give 89 mg (100% yield) of compound 4 as a TFA salt. $^1$H NMR (CDCl$_3$) δ 7.54

(br s, 1H, NH), 4.17 (s, 5H, Fc), 4.12 (s, 4H, Fc), 4.06 (m, 2H, CH$_2$), 3.35 (s, 2H, CH$_2$), 1.61 (br s, 2H, NH$_2$); $^{13}$C NMR (CDCl$_3$) δ 172.3 (C=O), 85.3 (1C, Fc), 68.7 (5C, Fc), 68.2 (4C, Fc), 44.8 (CH$_2$), 38.3 (CH$_2$); MS, electrospray ionization, m/z calcd for C$_{13}$H$_{17}$FeN$_2$O (M+H)$^+$ 273.1, found 273.4.

(S)-2-Amino-N-(2-[(ferrocenylmethyl)amino]-2-oxoethyl)-3-phenylpropanamide (6)

A solution of 65 mg (0.17 mmol) of compound 4 (TFA salt), 64 mg (0.24 mmol) of (S)—N-Boc-phenylalanine, 65 mg (0.53 mmol) of 4-(dimethylamino)pyridine (DMAP), and 92 mg (0.48 mmol) of EDC in 1 mL of DMF and 2 mL of dichloromethane was stirred under argon for 12 hours. The mixture was diluted with dichloromethane and water (50 mL each) and acidified with 2N HCl to pH=2. The organic layer was separated on a separatory funnel and the aqueous layer was extracted with dichloromethane four times. The combined organic layers were washed with brine, dried (anh. Na$_2$SO$_4$), concentrated, and column chromatographed on silica gel using a gradient mixture of hexane and ethyl acetate to give 48 mg (55% yield) of compound 5. $^1$H NMR (CDCl$_3$) δ 7.33-7.17 (m, 5H, Ph), 6.41 (br s, 2H, NH), 4.91 (br s, 1H, NH), 4.27 (q, J=7.0 Hz, CHN), 4.19-4.02 (m, 11H, Fc & CH$_2$), 3.87 (t, J=7 Hz, 2H, CH$_2$), 3.10 (dd, J=13.7, 7.0 Hz, 1H, CH$_2$Ph), 3.03 (dd, J=13.7, 7.0 Hz, 1H, CH$_2$Ph), 1.39 (s, 9H, t-Bu); MS, electrospray ionization, m/z calcd for C$_{27}$H$_{33}$FeN$_3$NaO$_4$ (M+Na)$^+$ 542.2, found 541.7.

A solution of 48 mg (92 μmol) of compound 5 in 4 mL of 20% TFA in dichloromethane was stirred at 25° C. for 90 minutes, and the solution was concentrated to dryness on a rotary evaporator to give 36 mg of the TFA salt of compound 6. It was diluted with 2 mL of water and neutralized with aqueous sodium bicarbonate to pH=6, and extracted with dichloromethane twice. The combined extracts were washed with brine, dried (MgSO$_4$), concentrated, and column chromatographed on silica gel using a gradient mixture of dichloromethane and methanol as an eluent to give 16 mg (57% yield) of compound 6. $^1$H NMR (CDCl$_3$) δ 7.95 (br s, 1H, NH), 7.34-7.21 (m, 3H, Ph), 7.20 (d, J=8 Hz, 2H, Ph), 6.47-6.51 (br s, 1H, NH), 4.17 (s, 5H, Fc), 4.12 (s, 4H, Fc), 4.10 (m, 2H, CH$_2$), 3.92 (d, J=4 Hz, 2H, CH$_2$), 3.65 (dd, J=8, 4 Hz, 1H, CHN), 3.25 (dd, J=16, 4 Hz, 1H, CH$_2$Ph), 2.70 (dd, J=16, 8 Hz, 1H, CH$_2$Ph), 1.53 (br s, 2H, NH$_2$); $^{13}$C NMR (CDCl$_3$) δ 175.4 (C=O), 168.6 (C=O), 137.8, 129.5, 129.0, 127.2, 84.7 (1C, Fc), 68.9 (5C, Fc), 68.4 (4C, Fc), 56.6, 43.6, 41.1, 39.1; MS, electrospray ionization, m/z calcd for C$_{22}$H$_{25}$FeN$_3$NaO$_2$ (M+Na)$^+$ 442.1, found 442.5.

Synthesis of H-Arg-Phe-Gly-NHCH$_2$-Fc (or (S)-2-amino-N—{(S)-1-[2-(ferrocenylmethylamino)-2-oxoethylamino]-1-oxo-3-phenylpropan-2-yl}-5-guanidinopentanamide) (10)

A CEM microwave peptide synthesizer was used to synthesize the tripeptide. The procedures for coupling, removal of Fmoc protecting group, and cleavage from the resin were identical to that described for the synthesis of legumain substrate [Swisher 2014, Bioses Bioelect]. From 1.52 g (0.73 mmol) of glycine chlorotrityl resin, 0.23 g (83% yield) of H-Arg-Phe-Gly-OH (9) was obtained as a white solid. MS, m/z, calcd for C$_{17}$H$_{27}$N$_6$O$_4$ (M+H)$^+$ 379.2, found 379.2.

To a solution of 75 mg (0.20 mmol) of H-Arg-Phe-Gly-OH (9) in 10 mL of dioxane and water (1:1) were added 60 μL of triethylamine and 88 mg (0.40 mmol) of di-tert-butyl dicarbonate. The resulting solution was stirred at 25° C. for 12 hours and concentrated to dryness to give 95 mg (99% yield) of Boc-Arg-Phe-Gly-OH: MS, electrospray ionization, m/z, calcd for C$_{22}$H$_{35}$N$_6$O$_6$ (M+H)$^+$ 479.3, found 479.0. The crude product was used in the subsequent step without purification. To a solution of 35 mg (73 μmol) of Boc-Arg-Phe-Gly-OH and 27 mg (73 μmol) of HATU in 1 mL of DMF under argon was added 16 mg (73 μmol) of (aminomethyl)ferrocene. The solution was stirred at 25° C. for 12 hours, filtered, and separated on a HPLC using a preparative column (Phenomenex-Jupiter C18) and eluting with 40% acetonitrile/water to 80% acetonitrile/water over 40 minutes with a 10 ml/min flow rate. The fractions containing the desired product were combined and lyophilized to yield Boc-Arg-Phe-Gly-NHCH$_2$-Fc as a yellow solid (15 mg; 32% yield). MS, m/z, calcd for C$_{33}$H$_{46}$FeN$_7$O$_5$ (M+H)$^+$ 676.3, found 676.3.

A solution of 15 mg (22 μmol) Boc-Arg-Phe-Gly-NHCH$_2$-Fc in 2 mL of 10% TFA in dichloromethane was stirred at 25° C. for 30 min, concentrated gently on a rotary evaporator, dissolved in deionized water (2 mL), frozen, and lyophilized to give H-Arg-Phe-Gly-NHCH$_2$-Fc as a solid, which was purified on HPLC using a gradient mixture of methanol and water as eluent to afford 6 mg (47% yield) of compound 10. $^1$H NMR (CDCl$_3$) δ 7.4-7.2 (m, 5H, Ph), 4.16 (s, 2H), 4.14 (s, 9H, Fc), 4.11 (s, 2H), 3.55 (s, 2H), 3.49 (s, 4H), 1.55 (br s, 9H, NH), 1.27-1.23 (m, 4H); MS, electrospray ionization, m/z, calcd for C$_{28}$H$_{38}$FeN$_7$O$_3$ (M–H)$^+$ 576.2, found 576.2.

Fabrication of VACNF NEAs

The fabrication procedures for the VACNF NEAs followed the protocols described above for Examples 1 and 2. Briefly, VACNFs with average length of ~5 μm were grown on Cr coated Si(100) wafer using plasma enhanced chemical vapor deposition (PECVD) system (Aixtron, Calif.). A nickel film with 22 nm thickness was coated as the catalyst for CNF growth. The diameter of the CNFs distributed from 100 to 250 nm and CNFs were well separated from each other with a distance of 0.5-2 μm, corresponding to a surface density of (3-50)×10$^7$ CNF tips per cm$^2$. Dielectric SiO$_2$ was deposited on the as-grown CNFs using chemical vapor deposition (CVD). Reactive ion etching (RIE) system (Nano-Master Inc., Austin, Tex.) was performed to selectively etch away desired amount of SiO$_2$. Only a length of ~20 nm to 300 nm of the longest CNFs were exposed by protruding over the SiO$_2$ matrix.

The VACNF NEA chip needed to be preconditioned before each use. The random VACNF NEAs were polished with 0.05-μm γ-alumina slurry on napless polishing cloth (Buehler, Lake Bluff, Ill.) for 5-15 mM, followed by rinsing with deionized water. The e-beam patterned regular VACNF NEA chip was treated with 30 s of O$_2$ reactive ion etching (RIE) (NANO-MASTER Inc, Austin, Tex.) to clean the chip surface and then followed by 4 mM of RIE with a mixture flow of CHF$_3$ and O$_2$ (at 10.0 and 2.0 sccm, respectively) to remove ~200 nm thickness of SiO$_2$. Both types of VACNF NEAs were then electrochemically activated by etching in 1.0M NaOH solution using four cycles of CV in a potential range of –0.10 V to 1.20 V (vs. Ag/AgCl (3M KCl)) at a scan rate of 50 mV·s$^{-1}$.

To reduce nonspecific adsorption of the biomolecules, the SiO$_2$ surface of the VACNF NEAs was first passivated with protective moieties containing ethylene glycol. The chip was immersed in an 8 g·L$^{-1}$ solution of APTES in ethanol for 20 mM to produce a primary amine derivatized surface. The chip was treated with 50 μL solution of 0.1 mM of 2-(2-methoxyethoxy)ethoxyacetic acid, 100 g·L$^{-1}$ of EDC and 50 g·L$^{-1}$ of sulfo-NHS, and incubated at 25° C. for 2 h in a closed chamber (Arrayit, Calif.). The carboxylic acid group of 2-(2-methoxyethoxy)ethoxyacetic acid formed an amide bond with the amino function on the chip surface, leaving ethylene glycol moiety at the top surface. The molecules attached to the CNF tips were then removed by electrochemical etching at 1.2 V (vs. Ag/AgCl (3M KCl)) for 20 s in 1.0M NaOH solution. This process regenerated clean CNF tips which contained abundant carboxylic acid functional groups.

The VACNFs were then activated by electrochemical pretreatments. The Fc-appended tetrapeptides were covalently linked to the VACNF NEA by forming an amide bond between the —(CH$_2$)$_4$NH$_2$ linker and the —COOH group at the exposed CNF tips. In order to stabilize electrochemical signals, the unreacted —COOH sites at the VACNF NEA was further reacted with 6-aminohexanol as diluent agents.

The Fc-appended tetrapeptides were covalently linked to the VACNF NEA through a —(CH$_2$)$_4$NH$_2$ linker by forming amide bond facilitated by 1-ethyl-3-(3-dimethylaminopropyl)carbodiimide hydrochloride (EDC) and sodium 1-hydroxy-2,5-dioxopyrrolidine-3-sulfonate (sulfo-NHS). Typically, a 10 µL solution consisting of 10 mM tetrapeptide mixed with 90 µL of 10 g·L$^{-1}$ EDC and 10 g·L$^{-1}$ sulfo-NHS was applied onto the electrochemically activated VACNF NEA chip and incubated in a closed Arrayit chamber at 25° C. for 2 h. Control experiments and HPLC-MS characterization confirmed that only the end —NH$_2$ group of the tetrapeptide formed amide bond with the carboxylic acid group on the VACNF NEA. The —NH$_2$ and NH functions of the guanidine group in arginine residue in the tetrapeptide did not react with the carboxylic acid group under the reaction conditions. In order to stabilize the electronic signal, the CNF electrode surface was further dipped into 5.0 mL solution containing a diluent agent (1.0 mM 6-amino-1-hexanol) and the coupling agents (5.0 g·L$^{-1}$ EDC, and 2.0 g·L$^{-1}$ sulfo-NHS) so that the unreacted —COOH sites were linked with 6-aminohexanol.

Electrochemical Measurements of Enzymatic Activity

The electrochemical measurements were performed in a TEFLON cell with a total volume of 250 µL and the cell was sealed against the VACNF NEA chip with a 3-mm i.d. O-ring. Three-electrode configuration was used in all measurements, including a VACNF NEA as working electrode, an Ag/AgCl (3M KCl) as reference electrode and a coiled Pt wire as counter electrode. The electrolyte solution was 25 mM MES (pH=5.0). The ACV was measured by applying a 800 Hz and 150 mV amplitude AC voltage on the DC staircase waveform sweeping from −0.1 V to +0.75 V at 10 mV•s$^{-1}$ scan rate.

Enzyme Activity Measurements with Fluorescence Assays

Cathepsin B specific fluorogenic peptide substrate benzyloxycarbonyl-leucine-arginine-7-amino-4-methylcoumarin (Z-Leu-Arg-AMC) (Bachem, Torrance, Calif.) was used in the fluorescence assay to measure enzyme activity. The cleavage at the site between arginine and AMC dye by cathepsin B resulted in the increase of fluorescence intensity.

Confirmation of Cleaving Product Using HPLC

H$_2$N—(CH$_2$)$_4$—CO-(SEQ ID NO:2)-NH—CH$_2$-Fc was incubated with cathepsin B in a 25 mM MES buffer (pH=5.0) solution for two hours at 25° C. The crude product was directly injected to HPLC using a preparative column (Phenomenex-Jupiter C18) and eluting with a gradient mixture of methanol and water (an increment from 10% to 90% methanol) over 50 min and a 10 ml/min flow rate. The cleavage product, Phe-Gly-NH—CH$_2$-Fc appeared at 37 min, was found confirming that the proteolysis took place at the arginine site. The identity of the 37-minute peak, Phe-Gly-NH—CH$_2$-Fc, was verified by its mass spectrum (MS) and HPLC retention time, which are identical with those of the authentic samples prepared independently (see Supplementary Material). Other possible cleavage by-products such as Arg-Phe-Gly-NH—CH$_2$-Fc and Gly-NH—CH$_2$-Fc were not found from the HPLC/MS analysis.

Western Blot and Immunoprecipitation of Cancer Cell Lysates

Cells were harvested and lyzed in lysis buffer (20 mM Tris pH 7.5, 0.5 mM EDTA, 0.5 mM EGTA, 0.5% Triton X-100) at 1:1,000 dilution of protease inhibitors (Sigma-Aldrich, Saint Louis, Mo.). Twenty-five µg of whole-cell extract was resolved by 10% SDS polyacrylamide gel electrophoresis (PAGE) and transferred to nitrocellulose membrane (Midwest Scientific, Saint Louis, Mo.). Nitrocellulose membrane was blocked in 5% milk for an hour at room temperature and then incubated with monoclonal antibodies (1:1,000). Western blots were detected by enhanced chemiluminescence detection reagents (Pierce, Rockford, Ill.) and visualized by Fluorchem E imaging system (ProteinSimple, Santa Clara, Calif.).

The procedure for obtaining whole cell extract for immunoprecipitation was the same as done in western blotting. One milligram of whole cell extract was used and pre-cleaned with protein A/G-agarose beads (Santa Cruz Biotechnology, Santa cruz, Calif., USA) for 30 minutes. Then, centrifuged at 2,000 rpm for 5 minutes and supernatant was collected and incubated with the primary antibody, cathepsin B (1:1000), overnight at 4° C. Samples were centrifuged at 2,000 rpm for 5 minutes and pellet was washed three times with lysis buffer. Samples were run on 10% SDS-PAGE and immunoblotted with cathepsin B as described in western blot analysis. In case of multiple steps of immunoprecipitation, samples were incubated with cathepsin B antibodies for 2 or 3 times prior to western blot analysis. This repeated step allows the complete removal of cathepsin B in whole cell lysate.

Cell Lines and Correlation with Cancer Stages

The selected cell lines were used in mimicking different cell patterns in breast cancer progression. HMECs, obtained from Lonza, are primary cells, derived from adult female breast tissue. HMECs are positive for cytokertins 14 and 18 and negative for cytokeratin 19. MCF-10A cell line, obtained from ATCC, is a non-tumorigenic epithelial cell line derived from a 36 year old female. These cells have no signs of terminal differentiation or senescence. They respond to insulin, epidermal growth factor (EGF), and glucorcorticoids. T47D cell line, obtained from ATCC, was isolated from a pleural effusion obtained from a 54 year old female patient with an infiltrating ductal carcinoma of the breast. MDA-MB-231 cell line, obtained from ATCC, was isolated from a metastatic site of a 51 year old female patient with breast adenocarcinoma.

Results

ACV Measurement of Proteolysis of Purified Cathepsin B

Figure 10:
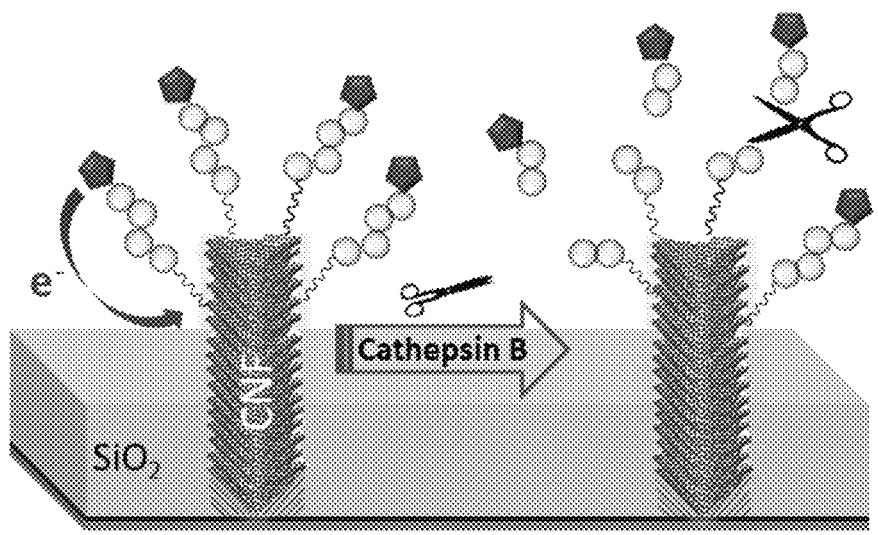
FIG. 10 is a schematic diagram of the cleavage of tetrapeptide $H_2N—(CH_2)_4$—CO-(SEQ ID NO:2)-NH—$CH_2$-Fc at the VACNF NEA tip by cathepsin B.
Figure 10:
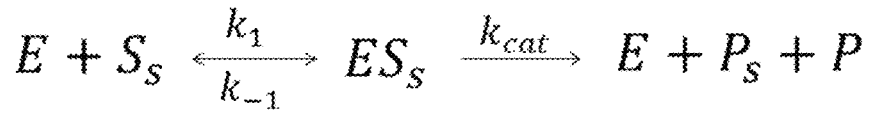

The schematic diagram of cleavage of tetrapeptide H$_2$N—(CH$_2$)$_4$—CO-(SEQ ID NO:2)-NH—CH$_2$-Fc attached on the CNF tips by cathepsin B is shown in FIG. 10. In ACV measurement, Fc attached to the CNFs provides a reliable oxidation peak at ~0.25 V versus Ag/AgCl (3M KCl). The AC peak current $i_{p,acv}$ can be obtained by subtracting the linear background. The value of $i_{p,acv}$ remained relatively stable before adding the enzyme. After adding cathepsin B, the tetrapeptide was cleaved at the site between arginine and phenylalanine. The fragment containing Fc was thus released into the bulk solution causing the peak current $i_{p,acv}$ to decrease. The kinetics of the proteolysis from purified cathepsin B was monitored by continuously repeated ACV measurements. The curve corresponding to cathepsin B proteolysis showed an exponential decay versus the reaction time, which can be fitted with Eq. 1 from Example 2, above. The proteolysis kinetics on the VACNF NEAs can be explained with modified Michaelis-Menten model of heterogeneous enzymatic reactions also described above in Example 2.

Western Blot Analysis and Immunoprecipitation Assay

Figure 11:
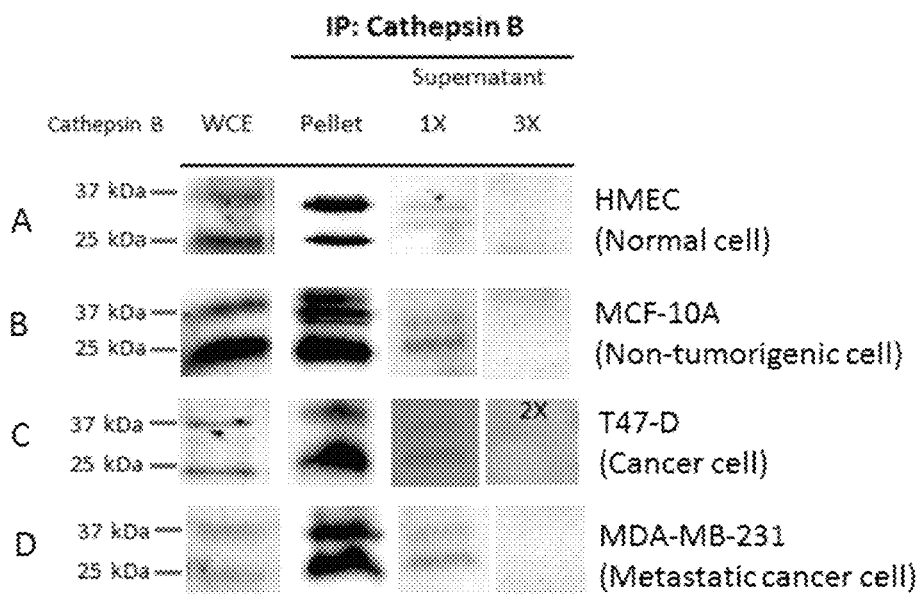
FIG. 11 illustrates the expression of cathepsin B in normal breast cells (HMEC), (A) illustrates non-tumorigenic breast cells (MCF-10A), (B) illustrates breast cancer cells (T47D), (C) illustrates metastatic breast cancer cells (MDA-MB-231), and (D) illustrates 0.5 mg of whole cell extract (WCE) that was used for immunoprecipitation assay using cathepsin B antibody.

The expression of cathepsin B in normal breast cells HMEC, non-tumorigenic breast cells MCF-10A, breast cancer cells T47D and metastatic cancer cells MDA-MB-231 was subjected to western blot analysis. The molecular weight of pro and active form of cathepsin B is ~37 kDa and ~25 kDa, respectively. After incubated in activation buffer consisting of 5 mM DTT and 25 mM MES, pro cathepsin B fully transformed to the active enzyme with ~25 kDa molecular weight. As illustrated in FIG. 11, cathepsin B in both pro and active forms was found in the whole cell extract of all breast cells. Cathepsin B was then precipitated out by using cathepsin B antibody, the procedure of which is called immunoprecipitation. The pellet, immunoprecipted fraction, was then subjected to western blot analysis. Qualitatively, total amount of cathepsin B in normal breast cells pellet seemed to be less than that in transformed and cancerous cell pellets, as shown in the intensity of the western blot. After one round of immunoprecipitation, detectable amount of cathepsin B was still present in the supernatant of the lysate. No obvious amount of cathepsin B was found in the supernatant after 2 to 3 times of immunoprecipitation, indicating a complete removal of cathespin B in the sample.

Electrochemical Study of Proteolysis of Breast Cancer Cell Lysates (MDA-MB-231)

The proteolysis of breast cancer cell lysate MDA-MB-231 and its cathepsin B-removed lysate by two rounds of immunoprecipitation has been studied electrochemically. The cathepsin B specific tetrapeptide $H_2N-(CH_2)_4-CO$-(SEQ ID NO:2)-$NH-CH_2$-Fc was immobilized on VACNF NEAs. The MDA-MB-231 cell lysate was first incubated in the activation buffer in order to transform all the cathepsin B into their active form (~25 kDa). A solution of 25 µL of the activated MDA-MB-231 lysate solution or the cathepsin B-removed lysate was then added into the electrochemical cell containing 250 µL of 25 mM MES (pH 5.0) while ACV signal from the Fc-appended tetrapeptide was repeatedly recorded. The final concentration of the MDA-MB-231 cell lysate and the cathepsin B-removed lysate was 7.275 µg·mL$^{-1}$. Adding both lysate samples caused kinetic exponential decay. The fitted time constants are $\tau_1$=215 s for MDA-MB-231 cell lysate (pink dots) and $\tau_2$=533 s for the cathepsin B-removed lysate (blue triangle). Cathepsin B-removed lysate showed much slower kinetic decay rate compared to the one without immunoprecipitation. In order to confirm the difference of decay rate is indeed due to the removal of cathepsin B, 15.5 nM cathepsin B was spiked into the 7.275 µg·mL$^{-1}$ cathepsin B-removed MDA-MB-231 lysate. A shorter decay time was observed with $\tau_3$=352 s, compared to $\tau_2$=533 s for non-spiking lysate. The value of $k_{cat}/K_M$ can be derived by Eq. 6 described in Example 2. The decay time constant $\tau$ is directly related to the protease activity.

Western Blot Analysis and Immunoprecipitation Assay

The expression of cathepsin B in normal breast cells HMEC, non-tumorigenic breast cells MCF-10A, breast cancer cells T47D and metastatic cancer cells MDA-MB-231 was subjected to western blot analysis. The molecular weight of pro and active form of cathepsin B is ~37 kDa and ~25 kDa, respectively. After incubated in activation buffer consisting of 5 mM DTT and 25 mM MES, pro cathepsin B fully transformed to the active enzyme with ~25 kDa molecular weight.[3] As illustrated in FIG. 2, cathepsin B in both pro and active forms was found in the whole cell extract of all breast cells. Cathepsin B was then precipitated out by using cathepsin B antibody, the procedure of which is called immunoprecipitation. The pellet, immunoprecipted fraction, was then subjected to western blot analysis. Qualitatively, total amount of cathepsin B in normal breast cells pellet seemed to be less than that in transformed and cancerous cell pellets, as shown in the intensity of the western blot. After one round of immunoprecipitation, detectable amount of cathepsin B was still present in the supernatant of the lysate. No obvious amount of cathepsin B was found in the supernatant after 2 to 3 times of immunoprecipitation, indicating a complete removal of cathespin B in the sample.

Electrochemical Study of Proteolysis of Breast Cancer Cell Lysates (MDA-MB-231)

The proteolysis of breast cancer cell lysate MDA-MB-231 and its cathepsin B-removed lysate by two rounds of immunoprecipitation has been studied electrochemically. The cathepsin B specific tetrapeptide $H_2N-(CH_2)_4-CO$-(SEQ ID NO:2)-$NH-CH_2$-Fc was immobilized on VACNF NEAs. The MDA-MB-231 cell lysate was first incubated in the activation buffer in order to transform all the cathepsin B into their active form (~25 kDa). A solution of 25 µL of the activated MDA-MB-231 lysate solution or the cathepsin B-removed lysate was then added into the electrochemical cell containing 250 µL of 25 mM MES (pH 5.0) while ACV signal from the Fc-appended tetrapeptide was repeatedly recorded. The final concentration of the MDA-MB-231 cell lysate and the cathepsin B-removed lysate was 7.275 µg·mL$^{-1}$. Adding both lysate samples caused kinetic exponential decay. The fitted time constants are $\tau_1$=215 s for MDA-MB-231 cell lysate and $\tau_2$=533 s for the cathepsin B-removed lysate. Cathepsin B-removed lysate showed much slower kinetic decay rate compared to the one without immunoprecipitation. In order to confirm the difference of decay rate is indeed due to the removal of cathepsin B, 15.5 nM cathepsin B was spiked into the 7.275 µg·mL$^{-1}$ cathepsin B-removed MDA-MB-231 lysate. A shorter decay time was observed with $\tau_3$=352 s, compared to $\tau_2$=533 s for non-spiking lysate. The value of $k_{cat}/K_M$ can be derived by:

$$(k_{cat}/K_M)\cdot([E_0]+15.5 \text{ nM})-(k_{cat}/K_M)\cdot[E_0]=1/\tau_3-1/\tau_2=0.96\times10^{-3} \text{ s}^{-1}, \quad (7)$$

which gives $k_{cat}/K_M$=6.19×10$^4$ M$^{-1}$s$^{-1}$. This value is slightly larger than 4.11×10$^4$ M$^{-1}$ s$^{-1}$ which derived from the purified cathepsin B. The difference of cathepsin B in MDA-MB-231 lysate and the cathepsin B-removed lysate can be obtained as follows:

$$(k_{cat}/K_M)\Delta E_0=1/\tau_1-1/\tau_2=2.77\times10^{-3} \text{ s}^{-1}. \quad (8)$$

Since $k_{cat}/K_M$=6.19×10$^4$ M$^{-1}$ s$^{-1}$ according to above calculation, the difference of cathepsin B in 7.275 µg·mL$^{-1}$ MDA-MB-231 lysate and cathepsin B-removed lysate is calculated as ~45 nM. To investigate whether our calculation is legitimate, we spiked 45 nM cathepsin B into 7.275 µg·mL$^{-1}$ cathepsin B-removed MDA-MB-231 lysate. A similar decay time, 207 s (versus $\tau_1$=215 s) was obtained. It was concluded that the immunoprecipitation procedure removed ~45 nM cathepsin B from 7.275 µg·mL$^{-1}$ MDA-MB-231 lysate.

The proteolysis of tetrapeptide $H_2N-(CH_2)_4-CO$-(SEQ ID NO:2)-$NH-CH_2$-Fc by different concentrations of MDA-MB-231 cell lysates was also studied. The decay rate was found to be increasing with the increasing concentrations of MDA-MB-231 lysates. The decay times are 53 s, 215 s and 410 s for 29.1, 7.275 and 2.425 µg·mL$^{-1}$ MDA-MB-231 cell lysates, respectively. According to Equation 6, $(k_{cat}/K_M)\cdot[E_0]$ can be represented by $1/\tau$ or the slope of $-dS/dt$ versus $S$. The values of $(k_{cat}/K_M)\cdot[E_0]$ derived from the slope were $1.86\times10^{-2}$, $4.60\times10^{-3}$ and $2.42\times10^{-3}$ s$^{-1}$ with lysate concentration at 29.1, 7.275 and 2.425 µg·mL$^{-1}$, respectively. The derived quantity $(k_{cat}/K_M)\cdot[E_0]$ is not perfectly linearly proportional to the lysate concentration $[E_0]$ but close. Importantly, the results confirmed that ACV method on VACNF NEAs is a reliable tool to quantitatively study the proteolysis of complex cell lysates.

Comparison of Proteolysis Kinetics of Different Breast Cell Lysates

One type of primary culture cells and three different breast cell lines were used to investigate whether VACNF NEAs could effectively detect cathepsin B in different breast cell lysates. Cathepsin B specific tetrapeptide H$_2$N—(CH$_2$)$_4$—CO-(SEQ ID NO:2)-NH—CH$_2$-Fc was used and immobilized on the VACNF NEAs. A solution of 25 µL of normal cell HMEC lysate, non-tumorigenic breast cell MCF-10A lysate, breast cancer cell T47D, or metastatic breast cell MDA-MB-231 lysates at concentration of 7.275 µg·mL$^{-1}$ was added into the electrochemical Teflon cell with 250 µL of 25 mM MES buffer (pH=5.0). The decay time is varied for different cell lysates. The decay times are 497, 311, 248 and 215 s for 7.275 µg·mL$^{-1}$ of HMEC, MCF-10A, T47D, and MDA-MB-231, respectively. The values of $(k_{cat}/K_M)\cdot[E_0]$ derived from the slope of $-dS/dt$ versus $S$ are $2.00\times10^{-3}$, $3.20\times10^{-3}$, $4.02\times10^{-3}$ and $4.60\times10^{-3}$ s$^{-1}$ accordingly.

Figure 12:
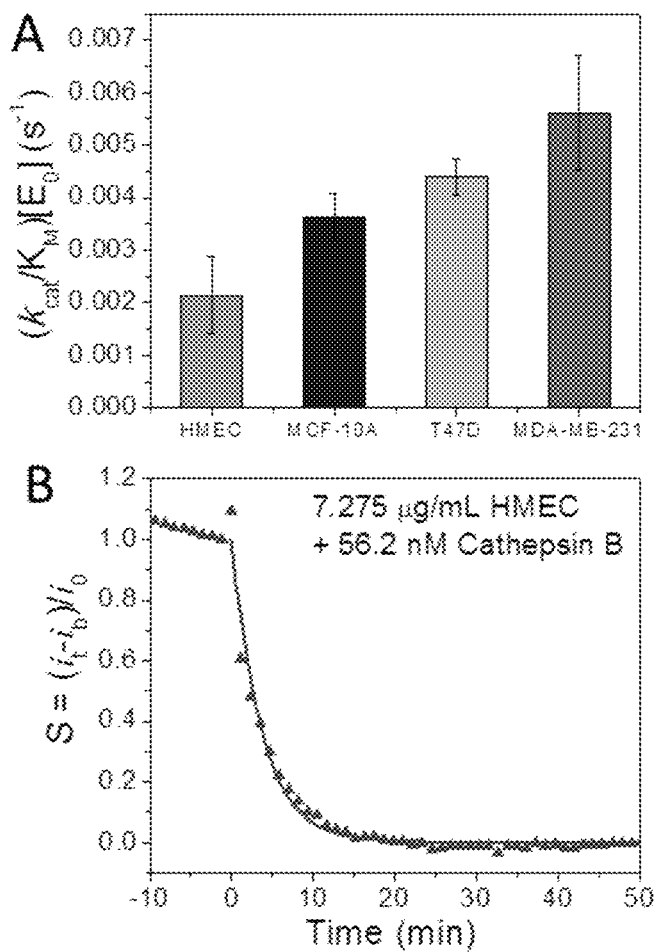
FIG. 12A is a comparison of the values of $(k_{cat}/K_M) \cdot [E_0]$ of different breast cell lysates in a bar graph.
FIG. 12B is a plot of the kinetic study of spiking 56.2 nM purified cathepsin B into 7.275 $μg·mL^{-1}$ HMEC.

Most of the early stage mammary tumors are ER-positive and many patients could respond to antiestrogen or endocrine therapy and later stage breast cancers become resistant to endocrine therapy and are more malignant, aggressive, invasive and metastatic. HMEC is derived from normal mammary tissue, and MCF-10A is a non-tumorigenic cell line, while T47D and MDA-MB-231 cell lines are derived from breast cancer patients. MDA-MB-231 has been shown to be estrogen receptor (ER)-negative, indicating a more aggressive form of breast cancer. Surprisingly, the electrochemical results showed that the values of $(k_{cat}/K_M)\cdot[E_0]$ ($=1/\tau$) are increasing with the increase in cancer progression. Comparison of the values of $(k_{cat}/K_M)\cdot[E_0]$ of different breast cell lysates in bar graph is shown in FIG. 12A. Triplicated experiments were carried out for each cell lysates. The values of $(k_{cat}/K_M)\cdot[E_0]$ are $(2.13\pm0.73)\times10^{-3}$, $(3.62\pm0.44)\times10^{-3}$, $(4.39\pm0.34)\times10^{-3}$ and $(5.61\pm1.09)\times10^{-3}$ s$^{-1}$ for HMEC, MCF-10A, T47D and MDA-MB-231 cell lysates at concentration of 7.275 µg·mL$^{-1}$, respectively.

In order to find out the overexpressed amount of cathepsin B in cancer cell lysates compared to the normal cells, the spiking experiment was done by spiking certain amount of cathepsin B into HMEC lysate solution. According to Equation 6, the difference of cathepsin B in HMEC and MCF-10A cell lysates at concentration of 7.275 µg·mL$^{-1}$ can be derived as:

$$(k_{cat}/K_M)\cdot\Delta E_0 = 3.62\times10^{-3} - 2.13\times10^{-3} = 1.49\times10^{-3} \text{ s}^{-1}. \quad (9)$$

Since $k_{cat}/K_M = 6.19\times10^4$ M$^{-1}$ s$^{-1}$ as obtained earlier, $\Delta E_0$ equals to 24.1 nM. This implied that 7.275 µg·mL$^{-1}$ HMEC spiked with 24.1 nM purified cathepsin B is equivalent to 7.275 µg·mL$^{-1}$ MCF-10A. Similarly, 7.275 µg·mL$^{-1}$ HMEC spiked with 56.2 nM purified cathepsin B is equivalent to 7.275 µg·mL$^{-1}$ MDA-MB-231 cell lysates according to the calculation. The kinetic study of spiking 56.2 nM purified cathepsin B into 7.275 µg·mL$^{-1}$ HMEC is shown in FIG. 12B. The decay time is 220 s. By repeating the experiment two more times, the statistic value of the decay time is $(255\pm30)$ s, and $(k_{cat}/K_M)\cdot[E_0]$ equals to $(3.97\pm0.50)\times10^{-3}$. This result illustrated that 7.275 µg·mL$^{-1}$ HMEC spiked with 56.2 nM cathepsin B is approximately equivalent to 7.275 µg·mL$^{-1}$ MCF-10A $((k_{cat}/K_M)\cdot[E_0]=(3.62\pm0.44)\times10^{-3}$ s$^{-1})$ instead of 7.275 µg·mL$^{-1}$ MDA-MB-231 as our previous calculation predicted. This result might imply that compared to the normal breast cell lysates, besides 24.2 nM more cathepsin B, there are other kinds of proteases equivalent to 32.1 nM cathepsin B (the difference between 24.2 nM and 56.2 nM) in 7.275 µg·mL$^{-1}$ transformed MCF-10A lysate.

Proteolysis study of breast cell lysates has also been studied by fluorescence method. Solutions of 0.05 mg·mL$^{-1}$ lysate of HMEC, MCF-10A, T47D and MDA-MB-231 were used in the fluorescence assay. The kinetic curves of the fluorescence intensity of breast cell lysates reacting with three different concentrations of substrate were plotted. Only the fluorescence intensity from the T47D lysate showed exponential increase which reflects the proteolytic kinetics of the proteases cleaving the substrate. The fluorescence intensity from HMEC lysate exhibited straight line instead of exponential curve while large noise due to extreme low signal was observed from the fluorescence assay of MCF-10A and MDA-MB-231 cell lysates. Thus, the fluorescence method was not able to determine the proteolytic kinetics of proteases from the complex cell lysates.

In this study, it has been shown that cathepsin B exists as both pro and mature forms in the whole cell extract of normal breast cells (HMEC), non-tumorigenic breast cells (MCF-10A) and breast cancer cells (T47D and MDA-MB-231). However, the results showed that western blot can only provide qualitative information without the ability to quantify the amount of protease in the breast cell samples. In addition, fluorescence assay failed to measure the proteolytic kinetics of the cathepsin B in the cell lysates. However, due to the complex components of the cancer cell lysates, the fluorescence intensity appeared to be oppressed by some unknown species in the cell lysates of MCF-10A and MDA-MB-231. In contrast, electrochemical method applied on VACNF NEAs has shown great potential and advantage to study the complex cell lysates quantitatively. We have shown that ACV measurements have been a reliable tool to derive the value of $(k_{cat}/K_M)\cdot[E_0]$ from the cancer cell lysate solution and the spiking experiments results matched well with the prediction from our calculation. This may due to the fact that well-separated protruding VACNF tips immobilized with the peptide substrate facilitate the protease to reach and cleave the specific site of the peptides. It was also found that the protease activity (i.e., the value of $(k_{cat}/K_M)\cdot[E_0]$) correlates with the progression stages of the cancer cells. The value of $(k_{cat}/K_M)\cdot[E_0]$ is highest for metastatic cancer cell MDA-MB-231, then followed by cancer cell T47D and non-tumorigenic cell MCF-10A. Normal cell lysate HMEC showed the smallest value of $(k_{cat}/K_M)\cdot[E_0]$, thus lowest protease activity.

In sum, the results suggested two critical features: 1) continuously repeated ACV measurement on VACNF NEAs has proved to be a reliable tool to quantify the protease activity in complex breast cell lysates; 2) the activity of cathepsin B measured by electrochemical method has been well correlated with the progression stages of the breast cancer cells. The method could be developed into a portable multiplex electronic system for cancer diagnosis and assessment of treatment efficacy.

Example 4

In this example, NEAs comprising VACNFs having two types of tetrapeptides specific to cancer-mediated proteases legumain and cathepsin B covalently attached to the exposed VACNF tip were utilized to measuring the activity of the target proteases in a fluid sample.

Apparatus and Reagents

The electrochemical measurements were conducted on a model 440A electrochemical analyzer (CH Instruments, Austin, Tex.). Fluorescence assay was performed on Glo-Max-Multi+Microplate Multimode Reader (Promega Corporation, Madison, Wis.). A 96-well black polystyrene plate in the fluorescent measurement was from Whatman (Picataway, N.J.). 3-Aminopropyl-triethoxysilane (APTES), 2-(2-methoxyethoxy)ethoxyacetic acid, 1-ethyl-3-(3-dimethyl-aminopropyl)carbodiimide hydrochloride (EDC), 1-hydroxy-2,5-dioxopyrrolidine-3-sulfonic acid sodium salt (sulfo-NHS), sodium hydroxides, and 6-amino-1-hexanol were purchased from Sigma-Aldrich (Saint Louis, Mo.). 2-(4-Morpholino)ethane sulfonic acid (MES) and dithiothreitol (DTT) were purchased from Thermo Fisher Scientific (Fair Lawn, N.J.). Recombinant human legumain/asparaginyl endopeptidase (molecular weight of 49 kDa) and recombinant human cathepsin B (molecular weight of 29 kDa) were acquired from R&D Systems Inc. (Minneapolis, Minn.). Before use for enzymatic reactions, legumain was activated in an activation buffer, comprising 50 mM $CH_3COONa$ (pH 4.0, adjusted by adding acetic acid) and 100 mM NaCl. Cathepsin B was activated in an activation buffer of 5 mM DTT and 25 mM MES (pH 5.0). Substrates Z-Ala-Ala-Asn-AMC and Z-Leu-Arg-AMC with Z=N-carbobenzyloxy and AMC=7-Amino-4-methylcoumarin for fluorescence assay were obtained from Bachem (Torrance, Calif.). All aqueous solutions were prepared using 18.2 $M\Omega$-cm resistivity deionized (DI) water from a benchtop water purifier (Barnstead EASYpure II RF/UV, Model D7035, Thermo Scientific, Asheville, N.C.).

Synthesis of Ferrocene-Appended Tetrapeptides for Enzyme Cleavage

Ferrocene-appended tetrapeptide for legumain cleavage (i.e., $H_2N$—$(CH_2)_4$—CO-(SEQ ID NO:1)-NH—$CH_2$-Fc) was synthesized following the sequence of reactions described in Example 1, above. Ferrocene-labeled tetrapeptide substrate for cathepsin B cleavage (i.e., $H_2N$—$(CH_2)_4$—CO-(SEQ ID NO:2)-NH—$CH_2$-Fc) was synthesized using a synthetic scheme similar to that described in Example 2, above.

Fabrication of VACNF NEAs

The NEAs were also fabricated as described in Example 1, above. The length of exposed CNF tips was controlled at ~50-300 nm by varying the RIE time to selectively remove $SiO_2$.

Electrode Preconditioning/Passivation of $SiO_2$ Surface

Before each use, VACNF NEAs were preconditioned as described in Example 1, above. In addition, the $SiO_2$ surface of the VACNF NEA chip was passivated as described in Example 1, above.

Functionalization of the VACNF NEA Chip

The tetrapeptide $H_2N$—$(CH_2)_4$—CO-(SEQ ID NO:1)-$NHCH_2$-Fc for legumain study or $H_2N$—$(CH_2)_4$—CO-(SEQ ID NO:2)-NH—$CH_2$-Fc for cathepsin B study was covalently linked to the VACNF NEA by forming amide bond facilitated by EDC and sulfo-NHS. Typically, a solution of 10 μL of 10 mM tetrapeptide mixed with 90 μL of 10 g L−1 EDC and sulfo-NHS was applied onto the electrochemically activated VACNF NEA chip and incubated in the enclosed Arrayit chamber at room temperature for 2 h. Control experiments and HPLC-MS characterization (see Supporting Information) confirmed that only the end —$NH_2$ group of the tetrapeptide formed amide bond with the carboxylic acid group on the VACNF NEA. The —$NH_2$ and —NH— functions in asparagine and arginine moieties in the peptide do not react with the carboxylic acid group under the reaction conditions. To stabilize the electronic signal, the CNF electrode surface was further dipped into a solution of 5 mL of 1 mM 6-amino-1-hexanol containing 5 g·L$^{-1}$ EDC and 2 g·L$^{-1}$ sulfo-NHS so that the unreacted —COOH sites were linked with 6-aminohexanol.

Electrochemical Measurements

The electrochemical measurements were performed in a TEFLON cell with a total volume of 250 μL. The cell was sealed against a VACNF NEA chip with a 3 mm i.d. O-ring in a three-electrode configuration with the VACNF NEA as the working electrode, an Ag/AgCl (3M KCl) reference electrode and a coiled Pt wire as the counter electrode. The electrolyte solutions were consisted of 50 mM MES (pH=5.0) and 250 mM NaCl for legumain experiment and 25 mM MES (pH=5.0) for cathepsin B experiment. The average AC current was measured by applying an AC voltage bias on the DC staircase waveform with the potential sweeping from −0.05 to +0.65 V for legumain experiment and −0.1 V to +0.75 V for cathepsin B experiment, both at 10 mV·s$^{-1}$ scan rate. The parameters including AC voltage amplitude and frequency were varied in specific experiments and specified as the results are presented in later sections.

Validation of the Enzyme Activities with Other Biochemical Methods

The activities of the enzymes vary significantly from batch to batch and are very sensitive to the environment and storage conditions. To reduce the errors, all enzymes were first validated with an established fluorescencebased biochemical method before each electrochemical experiment. The legumain activity was measured with a kinetic fluorescence assay using a commercial substrate Z-Ala-Ala-Asn-AMC which gave strong fluorescence after cleavage at the site between asparagine and AMC dye. The substrate Z-Leu-Arg-AMC was used in the fluorescence assay for cathepsin B activity measurement. The cleavage at the site between arginine and AMC dye released the AMC from quenching by the carbonyl group and showed increased fluorescence intensity.

Results and Discussion

The Fc moiety at the distal end provides a reliable redox signal at ~0.25 V versus Ag/AgCl (3M KCl) in ACV measurements. When supplied with the specific protease, the peptide was expected to be cleaved at the particular site. As a result, the Fc moiety was released from the electrode surface into the bulk solution, causing the redox signal to decrease. The kinetics of the enzymatic reaction at the electrode surface were monitored by continuously repeated ACV measurements.

The ACVs of a macro-GCE and a VACNF NEA, both functionalized with the tetrapeptide $H_2N$—$(CH_2)_4$—CO-(SEQ ID NO:1)-$NHCH_2$-Fc to be used for legumain study were compared. A peak current was observed at ~0.2 V versus Ag/AgCl (3M KCl) for both electrodes. The amplitude of the peak current density ($i_p$) in the ACVs with macro-GCE increased from ~1.0×10$^{-7}$ A·mm$^{-2}$ at 10 Hz to ~2.0×10$^{-7}$ A·mm$^{-2}$ at 40 Hz, but then dropped to zero at 1500 Hz. In the meantime, the background signal steadily increased from ~4.7×10$^{-7}$, to 1.8×10$^{-6}$ and 2.8×10$^{-6}$ A·mm$^{-2}$, respectively. In contrast, although the $i_p$ of ACV with VACNF NEAs was not measurable at 10 and 40 Hz, it rose clearly above the background at 1500 Hz, giving ~2.0×10$^{-8}$ A·mm$^{-2}$. VACNF NEAs allowed the Fc signal to be detected at much higher frequency. It is noteworthy that the current density was calculated with the geometric electrode surface area. The actual exposed CNF surface area in the VACNF NEA is more than ~100 times less than the geometric surface area. Hence, the real current density at the CNF tip is at least 10 times higher than that at the GCE. Generally, the electrochemical signal is very sensitive to the Fc-surface distance because the electron transfer rate decays exponentially versus the Fc-surface distance. Hence, electrochemical sensors based on redox reactions normally use linker molecules less than 2 nm in length. Here, the electron transfer on both GCEs and VACNF NEAs was not significantly affected by the tetrapeptide and the linker (with a fully extended length of ~2.5 nm).

ACV uses a sinusoidal AC voltage superimposed on a DC potential ramp for voltammetric measurements. It has advantages over commonly used DC-based CV, particularly for biosensors, due to the ability to amplify the electrochemical signal of small quantity of redox tags by shuffling the electron between the redox tag and the electrode many times. In general, the signal increases with AC frequency at low frequencies but is saturated and then decreases at higher frequencies. The optimum frequency for Fc through a short NH$_2$CH$_2$— linker was found to be 40 times higher than that on the macro-GCE. The optimum frequency which gave the maximum $i_p$ was 40 Hz for the GCE, but 1750 Hz for the VACNF NEA. Despite that both frequency values are about half of those with short NH$_2$CH$_2$— linker, the drastic difference between VACNF NEA and macro-GCE remained the same, that is, the optimum frequency on the VACNF NEA was ~40 times of that on the GCE. The higher applicable AC frequency at VACNF NEA afforded a larger ACV signal (i.e., $i_p$) and faster ACV measurements. Each ACV measurement was done in ~60-70 s. As a result, the kinetics of enzymatic cleavage can be monitored with continuously repeated ACV measurements at a temporal resolution of ~1 min.

The AC peak current density $i_{p,acv}$ can be extracted by subtracting the background (as a simple sloped straight line). These values were versus the AC frequency. The AC peak current density of the GCE shows a sharp peak with the maximum at ~40 Hz and a full width at half-maximum (fwhm) of 140 Hz. The current value approximately increases linearly with the AC frequency but drops rapidly as the AC frequency exceeds 40 Hz. In contrast, the maximum AC peak current density was observed at 1750 Hz on the VACNF NEA and the fwhm asymmetrically spread over 5000 Hz, indicating a large range of frequency that can be used.

The current density increases about linearly with the frequency up to ~1000 Hz. When the peak current density was plotted versus the logarithm of the AC frequency, the curves obtained with the GCE and the VACNF NEA show similar shape but with shifted peak frequency. It is noted that the ACV measurements were not stable with the GCE. The peak shape changed significantly in about 10 min, which limits the use of GCEs for the difference between the GCE and the VACNF NEA. The peak current density ($i_{p,acv}$) reached the highest value of ~1.5×10$^{-6}$ A·mm$^{-2}$ at the amplitude of 0.35 V for GCE, while the peak current density kept increasing at the amplitude up to 0.50 V for the VACNF NEA. However, for the VACNF NEA at amplitude larger than 0.15 V, the value of the peak current density deviated from the linear relationship and the raw ACV peak became broad and unstable. For this reason, amplitude at 0.15 V was chosen as the optimum working amplitude in all the following ACV measurements for legumain activity study. For cathepsin B study, the tetrapeptide H$_2$N—(CH$_2$)$_4$—CO-(SEQ ID NO:2)-NH—CH$_2$-Fc was immobilized on the VACNF NEA, giving very similar ACV properties with slightly different optimum AC frequency (800 Hz) and amplitude (0.15 V), respectively. These optimum parameters were used in the following kinetic study on cathepsin B activities.

The change of peak current ($i_{p,acv}$) over time during continuously repeated ACV measurements with Fc-linked tetrapeptide (H$_2$N—(CH$_2$)$_4$—CO-(SEQ ID NO:2)-NHCH$_2$-Fc) immobilized on a VACNF NEA was plotted. The initial signal was quite stable, with only slow drifting. At ~20 min, a solution of 25 μL of 9.8 ng·μL$^{-1}$ (338 nM) cathepsin B in the activation buffer was added into the electrochemical cell, giving a final enzyme concentration of 30.7 nM. Due to the disturbance to the electrolyte, the ACV peak current jumped up and then followed by an exponential decay. The ACV curve measured at 20 min, immediately after the cathepsin B solution was added, was plotted. A clear peak at around 0.25 V confirmed the immobilization of Fc-linked tetrapeptide on the electrode surface. The representative background-subtracted ACV curves corresponding to 0, 5, 10, 20, and 55 min, respectively, after adding the cathepsin B solution, were plotted and showed that the peak current decreased over time and the peak position slowly shifted from 0.27 to 0.18 V. Two control experiments were carried out and confirmed that the exponential decay in $i_{p,acv}$ was truly attributed to the kinetics of enzymatic cleavage of the peptide. First, 25 μL of blank activation buffer, that is, 5 mM DTT and 25 mM MES (pH 5.0), was added into the electrochemical cell prefilled with 250 μL of electrolyte (25 mM MES (pH 5.0)). The disturbance to the ACV signal was negligible in this process. Second, a solution of 25 μL of activation buffer containing deactivated cathepsin B (which was confirmed with the fluorescence assay) was added into the electrochemical cell in the similar way as in the first case. Neither case showed the characteristic exponential decay observed when the activated enzyme was introduced. It is clear that the exponential decay was due to enzymatic cleavage to the tetrapeptide substrate by cathepsin B.

The observed proteolysis kinetics was explained with a modified Michaelis-Menten model for heterogeneous enzymatic reactions.

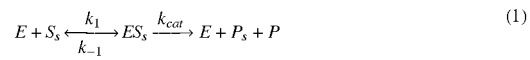

$$E + S_s \underset{k_{-1}}{\overset{k_1}{\longleftrightarrow}} ES_s \overset{k_{cat}}{\longrightarrow} E + P_s + P \quad (1)$$

where E, $S_s$, $ES_s$, $P_s$, and P represent the enzyme, the surfacebound peptide substrate, the enzyme-substrate complex on the electrode surface, the surface-attached product, and the product released to solution, respectively. The reaction rate can be defined as $$v = -\frac{d\Gamma_{Ss}}{dt} = \frac{d\Gamma_{Ps}}{dt} = \frac{k_{cat}[E_0] \times \Gamma_{Ss}}{K_m + [E_0]} \quad (2)$$

where $k_{cat}$ is the dissociation rate constant, $K_m = (k_{cat}+k_{-1})/k_1$ is the Michaelis-Menten constant, and $\Gamma_{Ss}$ and $\Gamma_{Ps}$ represent the surface densities of original and reacted peptide substrates, respectively. At low enzyme concentrations with [E$_0$]<<K$_m$, an approximate relationship can be obtained as $$v = -\frac{d\Gamma_{Ss}}{dt} = \frac{d\Gamma_{Ps}}{dt} = \frac{k_{cat}}{K_m}[E_0] \times \Gamma_{Ss} \quad (3)$$

The reaction rate υ (or $-d\Gamma_{Ss}/dt$) is a time-dependent quantity proportional to the change in electrochemical signals (dS/dt), where S is the kinetic electrochemical signal corresponding to the peak current $i_p$ in ACV measurements. As a result the slope of (dS/dt) versus the time-dependent $\Gamma_{Ss}$, will be equal to $(k_{cat}/K_m)[E_0]$, namely $$-\frac{d\Gamma_{Ss}/dt}{\Gamma_{Ss}} = -\frac{dS/dt}{S} = \frac{k_{cat}}{K_m}[E_0] \quad (4)$$

Thus, by rearranging the kinetic electrochemical data, we can derive the value of "specificity constant" $k_{cat}/K_m$, which is commonly used to represent the catalytic efficiency of enzymes.

To further analyze the kinetic enzymatic process, the peak current in ACV was converted into the quantity of surface adsorbed Fc (i.e., $\Gamma_{surf}$) based on $$i_{p,acv} = \left(\frac{2}{\pi}\right)\left(\frac{F^2}{4RT}\right)\Gamma_{surf}(2\pi f)V_0 \quad (5)$$

where the AC frequency f was 800 Hz and the amplitude of the AC voltage $V_0$ was 150 mV. Although the $\Gamma_{surf}$ value derived with eq 5 is known to be smaller than that obtained with other methods, particularly at high frequencies, the linear relationship between $i_{p,acv}$ and $\Gamma_{surf}$ remains true. The deviation of the proportional coefficient from the true value is canceled in later steps and does not affect the final results. The kinetic data can be fitted with an exponential decay superimposed on a linear curve corresponding to the slow baseline drift. The fitting equation is $$\Gamma_{surf} = 1.55 \times 10^{-15} \times e^{(-t/683.6)} - 2.19 \times 10^{-19}t + 1.38 \times 10^{-15} \quad (6)$$

From eq. 6, the reaction rate $v_i$ at different $\Gamma_{surf}$ can be calculated. The results of this calculation appeared to be a linear curve in the high $\Gamma_{surf}$ region. This linear curve is fitted by equation $$v_i = 1.15 \times 10^{-3}\Gamma_{surf} - 1.20 \times 10^{-18} \quad (7)$$

As mentioned earlier, both 12, and $\Gamma_{surf}$ are proportional to $i_{p,acv}$. The slope of $v_i$ versus $\Gamma_{surf}$, however, is independent of the exact proportional coefficient since it presented in both vi and $\Gamma_{surf}$ and is thus canceled. Therefore, we can derive the exact slope without being affected by the ACV experimental conditions. Equation 7 gives a slope of $1.15 \times 10^{-3}$ s$^{-1}$, which equals to $(k_{cat}/K_m)[E_0]$ as described in eq 3. With $[E_0]$=30.7 nM, the value of the "specificity constant" $k_{cat}/K_m$ can be calculated as $3.8 \times 10^4$ M$^{-1}$ s$^{-1}$. This value is close to the value of $2.3 \times 10^4$ M$^{-1}$ s$^{-1}$ derived from the comprehensive analysis with the fluorescence assay in a series of peptide substrate concentrations. It is also within the range reported in literature which varies from $\sim 2 \times 10^3$ M$^{-1}$ s$^{-1}$ to $\sim 7 \times 10^6$ M$^{-1}$ s$^{-1}$.

The ACV measurements with $H_2N$—$(CH_2)_4$—CO-(SEQ ID NO:1)-NH—$CH_2$-Fc immobilized on a VACNF NEA were plotted. Comparing to cathepsin B, the change of peak current corresponding to the cleavage by legumain was smaller, likely due to the difference in the enzyme activity. None of the two control experiments by adding the blank activation buffer and the buffer containing deactivated legumain (confirmed with fluorescence assay), respectively, showed the characteristic exponential decay in $i_{p,acv}$. The former caused negligible disturbance to the electrochemical signal. The latter caused the $i_{p,acv}$ to slowly rise by ~5% after 5 min and then became stabilized, which might be attributed to the disturbance to the tetrapeptide conformation on the electrode surface.

The data pertaining to reduction of the quantity of surface adsorbed Fc, $\Gamma_{surf}$, was fitted with the following equation:

$$\Gamma_{surf} = 3.23 \times 10^{-16} \times e^{(-t/1101)} - 4.36 \times 10^{-20}t + 3.75 \times 10^{-15} \quad (8)$$

where the time constant is 1101 s (~48 min), indicating that the reaction is quite slow. It normally took ~1 h to complete the kinetic measurement. This was found to be limited by the low enzymatic activity of legumain. However, it was still possible to extract the faradaic signal of Fc from the varying background with the ACV measurements. The plot of reaction rate ($v_i$) vs. the quantity of surface adsorbed Fc, $\Gamma_{surf}$, during the enzymatic reaction gave a linear curve fitted by equation $v_i = 6.30 \times 10^{-4}\Gamma_{surf} - 2.30 \times 10^{-18}$ with the slope of $6.30 \times 10^{-4}$ s$^{-1}$ at $[E_0]$=80.1 nM. From this analysis, the value of the $k_{cat}/K_m$ can be calculated as $7.9 \times 10^3$ M$^{-1}$ s$^{-1}$. This value is higher than the value of $4.3 \times 10^3$ M$^{-1}$ s$^{-1}$ derived from the comprehensive analysis using the fluorescence assay and the specifications provided by the vendor (R&D Systems).

The kinetic measurements with ACV for both cathepsin B and legumain were repeated at least three times under similar conditions, and the results were consistent and reproducible. Table 2 summarizes the statistical values of the specificity constant $k_{cat}/K_m$ derived from both electrochemical method using ACVs on VACNF NEAs in comparison with the fluorescence assay based on a series of substrate concentrations in solution, for both legumain and cathepsin B.

TABLE 2

| Enzyme | Peptide Sequence | $k_{cat}/K_M$ (M$^{-1}$s$^{-1}$) |
|---|---|---|
| Legumain | (FL$^a$) Ala-Ala-Asn---AMC | (4.3 ± 0.6) × 10$^3$ |
|  | (EC$^b$) Ala-Ala-Asn---Leu-NH—CH$_2$-Fc (SEQ ID NO: 1) | (11.3 ± 3.8) × 10$^3$ |
| Cathepsin B | (FL) Leu-Arg---AMC | (2.3 ± 1.7) × 10$^4$ |
|  | (EC) Leu-Arg---Phe-Gly-NH—CH$_2$-Fc (SEQ ID NO: 2) | (4.3 ± 0.8) × 10$^4$ |

Summary of the specificity constant $k_{cat}/K_M$ for legumain and cathepsin B, derived from electrochemistry (EC) by VACNF-NEAs and the fluorescence assay (FL). Dashed line indicates the cleave site.

Interestingly, the electrochemical method gave higher $k_{cat}/K_m$ values for both of legumain and cathepsin B than the fluorescence assay. In contrast, other studies using macroscopic electrodes found that the electrochemically measured $k_{cat}/K_m$ was normally lower than solution based assays, primarily due to the steric effects which lower the access of enzyme to the peptides attached to the flat surface. The results confirmed that the small radius in VACNF NEAs helped to eliminate the steric hindrance. The peptide substrates for the fluorescence assay consisted of only 3 and 2 amino acids, respectively, which were also expected to have lower binding affinity than the tetrapeptides used for our electrochemical measurements.

The values of the specificity constant kcat/Km for cathepsin B by both electrochemical and fluorescence assays are about 5 times of that of legumain. For ACV measurements, this helps to reduce the time constant for the exponential decay and makes the experiment easier and more reliable. As a result, lower enzyme concentration can be measured. From these results, it can be concluded that the ACV would work even better for measuring proteases with the $k_{cat}/K_m$ values higher than ~$4 \times 10^4$ $M^{-1}$ $s^{-1}$. But even proteases with relatively low specificity constant (such as legumain and cathepsin B) can still be reliably measured. Even though the required enzyme concentration was ~5 to 10 times higher than that by the fluorescence assay, the electrochemical method has a potential advantage that simultaneous detection of multiple proteases in a small volume is possible, attributed to its localized sensing mechanism using surface-attached peptides.

It is noteworthy that the $k_{cat}/K_m$ values of legumain and cathepsin B are relatively low, but they have high biological significance respect to cancer diagnosis and treatment. The speed and required enzyme concentration in the electrochemical measurements can be significantly improved when this technique is used to detect other proteases with higher $k_{cat}/K_m$ values, such as trypsin at $(1.44\pm0.1)\times10^6$ $M^{-1}$ $s^{-1}$, α-thrombin at $(1.0\pm0.2)\times10^6$ $M^{-1}$ $s^{-1}$, and plasmin at $6.7\times10^5$ $M^{-1}$ $s^{-1}$.

In previous electrochemical detection of proteases including trypsin, α-thrombin, and plasmin, normal CV measurements on gold electrodes were used. This method was found not applicable on carbon electrode. The Fc redox waves of the labeled tetrapeptide can be observed on the GCE, but the baseline currents were quite high, making it difficult to reliably extract redox signals. The previous studies on gold electrodes were able to block the nonfaradaic background current using close-packed, self-assembled monolayer of small passivating alkane thiol molecules. The covalent bond of small passivating molecules does not allow them to move around to form a close-packed monolayer. Thus, there were many leaking pinholes in the passivation layer on GCE. This is even more severe on VACNF NEA due to the curvature and inhomogeneity at the CNF surface. As a result, it was not possible to use CV to measure the Fc signal on VACNF NEAs. ACV provides a necessary solution for the reported enzymatic study.

In summary, it has been demonstrated that high-frequency ACV can be applied on embedded VACNF NEAs to measure the redox reaction of Fc attached to the exposed CNF tip through a tetrapeptide and linker molecule. Due to the additional capacitive current pathway enabled by the unique interior graphitic microstructure of the VACNFs, the optimum frequency giving the highest peak AC current for Fc on VACNF NEA was found to be 40 times that on GCEs. The higher frequency afforded a larger ACV signal and shorter time for the each ACV measurements. Thus, the kinetics of proteolysis of the surface-attached peptides can be measured upon addition of two types of cancer-related proteases, that is, legumain and cathepsin B. The kinetic process can be analyzed with a heterogeneous Michaelis-Menten model to derive the "specificity constant" $k_{cat}/K_m$, which is $(4.3\pm0.8)\times10^4$ $M^{-1}$ $s^{-1}$ for cathepsin B and $(1.13\pm0.38)\times10^4$ $M^{-1}$ $s^{-1}$ for legumain. These values are about two times of that measured with a fluorescence assay as well as the specifications provided by the vendor. The nanostructured electrode size clearly eliminated the steric effects for enzymatic reactions with surface-attached peptides. These VACNF NEA based electrochemical enzymatic biosensors can be developed into portable multiplex electronic devices for rapid cancer diagnosis and treatment monitoring.

---

We claim:

1. A nanoelectrode array comprising a substrate having a plurality of carbon nanofibers extending vertically therefrom, said nanofibers comprising a proximal end that is attached to said substrate and a distal end that is spaced apart from said substrate, said distal end of at least one of said nanofibers comprising a peptide or peptide residue covalently attached thereto, said peptide or peptide residue having a free end that is not bound to said nanofiber, said free end comprising a redox moiety attached thereto, said array being configured to detect the activity of one or more enzymes present within a biological sample through cleavage of said peptide or peptide residue by said one or more enzymes which releases said redox moiety from said array effecting a change in an electrical current across said array.

2. The array according to claim 1, wherein said nanofibers are encapsulated, except for at least one of said distal ends, within a matrix of an insulative material.

3. The array according to claim 2, wherein said insulative material comprises silicon dioxide.

4. The array according to claim 1, wherein said peptide or peptide residue is capable of being cleaved by a protease enzyme that is overexpressed by a cancer-causing cell.

5. The array according to claim 4, wherein said peptide is a tetrapeptide selected from the group consisting of Ala-Ala-Asn-Leu (SEQ ID NO:1), Leu-Arg-Phe-Gly (SEQ ID NO:2), and Pro-Leu-Ser-Leu (SEQ ID NO:3).

6. The array according to claim 1, wherein said peptide or peptide residue is a ferrocenyl peptide or ferrocenyl peptide residue.

7. The array according to claim 1, wherein said peptide or peptide residue is attached to said distal end by a linker molecule having an amine functional group.

8. The array according to claim 1, wherein said substrate is electrically conductive.

9. An electronic chip comprising a plurality of the nanoelectrode arrays according to claim 1.

10. The electronic chip according to claim 9, wherein said chip comprises at least two individually addressed nanoelectrode array in which a first peptide or peptide residue is attached to at least one of said carbon nanofibers of one of the nanoelectrode arrays, and a second peptide or peptide residue is attached to at least one of said carbon nanofibers of the other of said nanoelectrode arrays, said chip being operable to detect the presence of at least two different proteases contained within a biological sample brought into contact therewith.

11. The array according to claim 1, wherein said redox moiety comprises an organometallic moiety.

* * * * *

SEQUENCE LISTING

<160> NUMBER OF SEQ ID NOS: 5

<210> SEQ ID NO 1
<211> LENGTH: 4
<212> TYPE: PRT
<213> ORGANISM: Artificial Sequence
<220> FEATURE:
<223> OTHER INFORMATION: Synthesized peptide substrate

<400> SEQUENCE: 1

Ala Ala Asn Leu
1

<210> SEQ ID NO 2
<211> LENGTH: 4
<212> TYPE: PRT
<213> ORGANISM: Artificial Sequence
<220> FEATURE:
<223> OTHER INFORMATION: Synthesized peptide substrate

<400> SEQUENCE: 2

Leu Arg Phe Gly
1

<210> SEQ ID NO 3
<211> LENGTH: 4
<212> TYPE: PRT
<213> ORGANISM: Artificial Sequence
<220> FEATURE:
<223> OTHER INFORMATION: Synthesized peptide substrate

<400> SEQUENCE: 3

```
Pro Leu Ser Leu
1

<210> SEQ ID NO 4
<211> LENGTH: 16
<212> TYPE: PRT
<213> ORGANISM: Artificial Sequence
<220> FEATURE:
<223> OTHER INFORMATION: Synthesized peptide substrate

<400> SEQUENCE: 4

Ala Glu Glu Glu Ile Tyr Gly Glu Phe Glu Ala Lys Lys Lys Lys Cys
1               5                   10                  15

<210> SEQ ID NO 5
<211> LENGTH: 4
<212> TYPE: PRT
<213> ORGANISM: Artificial Sequence
<220> FEATURE:
<223> OTHER INFORMATION: Sythesized peptide substrate

<400> SEQUENCE: 5

Leu Asn Phe Gly
1
```